US011400161B2

(12) United States Patent
Cedillo et al.

(10) Patent No.: US 11,400,161 B2
(45) Date of Patent: Aug. 2, 2022

(54) METHOD OF CONJUGATING OLIGOMERIC COMPOUNDS

(71) Applicant: Ionis Pharmaceuticals, Inc., Carlsbad, CA (US)

(72) Inventors: Isaiah E. Cedillo, Vista, CA (US); Recaldo Carty, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/332,660

(22) PCT Filed: Oct. 6, 2017

(86) PCT No.: PCT/US2017/055481
§ 371 (c)(1),
(2) Date: Mar. 12, 2019

(87) PCT Pub. No.: WO2018/067900
PCT Pub. Date: Apr. 12, 2018

(65) Prior Publication Data
US 2021/0283263 A1 Sep. 16, 2021

Related U.S. Application Data

(60) Provisional application No. 62/515,329, filed on Jun. 5, 2017, provisional application No. 62/404,916, filed on Oct. 6, 2016.

(51) Int. Cl.
A61K 47/54 (2017.01)
A61K 47/56 (2017.01)
C07H 15/04 (2006.01)

(52) U.S. Cl.
CPC ............ A61K 47/549 (2017.08); A61K 47/56 (2017.08); C07H 15/04 (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,415,732 A | 11/1983 | Caruthers et al. |
| 4,458,066 A | 7/1984 | Caruthers et al. |
| 4,469,863 A | 9/1984 | Ts'o et al. |
| 4,476,301 A | 10/1984 | Imbach et al. |
| 4,500,707 A | 2/1985 | Caruthers et al. |
| 4,668,777 A | 5/1987 | Caruthers et al. |
| 4,725,677 A | 2/1988 | Koster et al. |
| 4,751,219 A | 6/1988 | Kempen et al. |
| 4,845,205 A | 7/1989 | Huynh Dinh et al. |
| 4,973,679 A | 11/1990 | Caruthers et al. |
| 4,981,957 A | 1/1991 | Lebleu et al. |
| 5,013,830 A | 5/1991 | Ohutsuka et al. |
| 5,023,243 A | 6/1991 | Tullis |
| 5,034,506 A | 7/1991 | Summerton et al. |
| 5,118,800 A | 6/1992 | Smith et al. |
| 5,130,302 A | 7/1992 | Spielvogel et al. |
| 5,132,418 A | 7/1992 | Caruthers et al. |
| 5,134,066 A | 7/1992 | Rogers et al. |
| RE34,036 E | 8/1992 | McGeehan |
| RE34,069 E | 9/1992 | Koster et al. |
| 5,149,797 A | 9/1992 | Pederson et al. |
| 5,166,315 A | 11/1992 | Summerton et al. |
| 5,175,273 A | 12/1992 | Bischofberger et al. |
| 5,177,196 A | 1/1993 | Meyer, Jr. et al. |
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,214,134 A | 5/1993 | Weis et al. |
| 5,216,141 A | 6/1993 | Benner |
| 5,220,007 A | 6/1993 | Pederson et al. |
| 5,223,618 A | 6/1993 | Cook et al. |
| 5,235,033 A | 8/1993 | Summerton et al. |
| 5,256,775 A | 10/1993 | Froehler |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |

(Continued)

FOREIGN PATENT DOCUMENTS

WO  WO 1994/002499  2/1994
WO  WO 1994/017093  8/1994

(Continued)

OTHER PUBLICATIONS

Krotz, Organic Process Research & Development 2004, 8, 852-858).. (Year: 2004).*
U.S. Appl. No. 60/989,574, filed Nov. 21, 2007, Seth et al.
U.S. Appl. No. 61/026,995, filed Feb. 7, 2008, Bhat et al.
U.S. Appl. No. 61/026,998, filed Feb. 7, 2008, Seth et al.
U.S. Appl. No. 61/056,564, filed May 28, 2008, Seth et al.
U.S. Appl. No. 61/086,231, filed Aug. 5, 2008, Migawa et al.
U.S. Appl. No. 61/097,787, filed Sep. 17, 2008, Seth et al.
U.S. Appl. No. 61/099,844, filed Sep. 24, 2008, Seth et al.
Abifadel et al., "Mutations in PCSK9 cause autosomal dominant hypercholesterolemia." Nat Genet. (2003) 34(2): 154-156.

(Continued)

Primary Examiner — Layla D Berry
(74) Attorney, Agent, or Firm — McNeill Baur PLLC

(57) ABSTRACT

Provided herein are solid phase methods for the synthesis of conjugated oligomeric compounds and intermediates used in such methods. In particular, the solid phase methods provide for addition of a phosphoramidite functionalized conjugate group to a solid support bound oligomeric compound. The methods also provide an increase in overall yield and a cost benefit over existing methods.

20 Claims, No Drawings
Specification includes a Sequence Listing.

(56) References Cited

U.S. PATENT DOCUMENTS

| | | |
|---|---|---|
| 5,359,044 A | 10/1994 | Cook et al. |
| 5,366,878 A | 11/1994 | Pederson et al. |
| 5,367,066 A | 11/1994 | Urdea et al. |
| 5,378,825 A | 1/1995 | Cook et al. |
| 5,386,023 A | 1/1995 | Sanghvi et al. |
| 5,393,878 A | 2/1995 | Leumann |
| 5,399,676 A | 3/1995 | Froehler |
| 5,403,711 A | 4/1995 | Walder et al. |
| 5,405,938 A | 4/1995 | Sumerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmelner et al. |
| 5,457,191 A | 10/1995 | Cook et al. |
| 5,459,255 A | 10/1995 | Cook et al. |
| 5,466,677 A | 11/1995 | Baxter et al. |
| 5,466,786 A | 11/1995 | Burh et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddty et al. |
| 5,563,253 A | 10/1996 | Agrawal et al. |
| 5,565,350 A | 10/1996 | Kmiec |
| 5,565,555 A | 10/1996 | Froehler et al. |
| 5,567,811 A | 10/1996 | Mistura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,587,470 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bishofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci |
| 5,652,355 A | 7/1997 | Metelev et al. |
| 5,652,356 A | 7/1997 | Agrawal |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,698,685 A | 12/1997 | Summerton et al. |
| 5,700,920 A | 12/1997 | Altmann et al. |
| 5,700,922 A | 12/1997 | Cook |
| 5,721,218 A | 2/1998 | Froehler |
| 5,750,692 A | 5/1998 | Cook et al. |
| 5,763,588 A | 6/1998 | Matteucci et al. |
| 5,792,608 A | 8/1998 | Swaminathan et al. |
| 5,792,847 A | 8/1998 | Burh et al. |
| 5,801,154 A | 9/1998 | Baracchini et al. |
| 5,808,027 A | 9/1998 | Cook et al. |
| 5,830,653 A | 11/1998 | Froehler et al. |
| 5,859,221 A | 1/1999 | Cook et al. |
| 5,948,903 A | 9/1999 | Cook et al. |
| 5,994,517 A | 11/1999 | Ts'o et al. |
| 5,998,203 A | 12/1999 | Matulic-Adamic |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,300,319 B1 | 10/2001 | Manoharan |
| 6,383,812 B1 | 5/2002 | Chen et al. |
| 6,426,220 B1 | 7/2002 | Bennett et al. |
| 6,525,031 B2 | 2/2003 | Manoharan |
| 6,525,191 B1 | 2/2003 | Ramasamy |
| 6,531,584 B1 | 3/2003 | Cook et al. |
| 6,582,908 B2 | 6/2003 | Fodor et al. |
| 6,600,032 B1 | 7/2003 | Manoharan et al. |
| 6,620,916 B1 | 9/2003 | Takahara et al. |
| 6,660,720 B2 | 12/2003 | Manoharan et al. |
| 6,670,461 B1 | 12/2003 | Wengel et al. |
| 6,727,064 B2 | 4/2004 | Karras |
| 6,770,748 B2 | 8/2004 | Imanishi et al. |
| 6,794,499 B2 | 9/2004 | Wengel et al. |
| 6,906,182 B2 | 6/2005 | Ts'o et al. |
| 6,908,903 B1 | 6/2005 | Theodore et al. |
| 7,015,315 B1 | 3/2006 | Cook et al. |
| 7,034,133 B2 | 4/2006 | Wengel et al. |
| 7,053,207 B2 | 5/2006 | Wengel |
| 7,101,993 B1 | 9/2006 | Cook et al. |
| 7,259,150 B2 | 8/2007 | Crooke et al. |
| 7,262,177 B2 | 8/2007 | Ts'o et al. |
| 7,399,845 B2 | 7/2008 | Seth et al. |
| 7,399,853 B2 | 7/2008 | Freier et al. |
| 7,425,544 B2 | 9/2008 | Dobie et al. |
| 7,427,672 B2 | 9/2008 | Imanishi et al. |
| 7,439,043 B2 | 10/2008 | DeFrees et al. |
| 7,491,805 B2 | 2/2009 | Vargeese et al. |
| 7,547,684 B2 | 6/2009 | Seth et al. |
| 7,563,884 B2 | 7/2009 | Cowsert et al. |
| 7,569,686 B1 | 8/2009 | Bhat et al. |
| 7,582,744 B2 | 9/2009 | Manoharan et al. |
| 7,598,227 B2 | 10/2009 | Crooke et al. |
| 7,666,854 B2 | 2/2010 | Seth et al. |
| 7,696,345 B2 | 4/2010 | Allerson et al. |
| 7,723,509 B2 | 5/2010 | Manoharan et al. |
| 7,741,457 B2 | 6/2010 | Swayze et al. |
| 7,750,131 B2 | 7/2010 | Seth et al. |
| 7,750,142 B2 | 7/2010 | Freier |
| 7,851,615 B2 | 12/2010 | Manoharan et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,080,644 B2 | 12/2011 | Wengel et al. |
| 8,084,437 B2 | 12/2011 | Freier et al. |
| 8,088,746 B2 | 1/2012 | Seth et al. |
| 8,088,904 B2 | 1/2012 | Swayze et al. |
| 8,093,222 B2 | 1/2012 | Freier et al. |
| 8,101,743 B2 | 1/2012 | Brown-Driver et al. |
| 8,106,022 B2 | 1/2012 | Manoharan et al. |
| 8,124,745 B2 | 2/2012 | Allerson et al. |
| 8,137,695 B2 | 3/2012 | Rozema et al. |
| 8,143,230 B2 | 3/2012 | Bhanot et al. |
| 8,153,365 B2 | 4/2012 | Wengel et al. |
| 8,158,601 B2 | 4/2012 | Chen et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |

(56) References Cited

U.S. PATENT DOCUMENTS

| | | |
|---|---|---|
| 8,313,772 B2 | 11/2012 | Rozema et al. |
| 8,344,125 B2 | 1/2013 | Manoharan et al. |
| 8,349,308 B2 | 1/2013 | Yurkovetskiy et al. |
| 8,404,862 B2 | 3/2013 | Manoharan et al. |
| 8,435,491 B2 | 5/2013 | Wang et al. |
| 8,440,803 B2 | 5/2013 | Swayze et al. |
| 8,450,467 B2 | 5/2013 | Manoharan et al. |
| 8,501,805 B2 | 8/2013 | Seth et al. |
| 8,501,930 B2 | 8/2013 | Rozema et al. |
| 8,507,661 B2 | 8/2013 | Manoharan et al. |
| 8,530,640 B2 | 9/2013 | Seth et al. |
| 8,541,548 B2 | 9/2013 | Rozema |
| 8,546,556 B2 | 10/2013 | Seth et al. |
| 8,552,163 B2 | 10/2013 | Lee et al. |
| RE44,779 E | 2/2014 | Imanishi et al. |
| 8,664,190 B2 | 3/2014 | Freier et al. |
| 8,673,632 B2 | 3/2014 | Crooke et al. |
| 8,828,956 B2 | 9/2014 | Manoharan et al. |
| 9,005,906 B2 | 4/2015 | Swayze et al. |
| 9,012,421 B2 | 4/2015 | Migawa et al. |
| 9,127,276 B2 | 8/2015 | Prakash et al. |
| 9,290,760 B2 | 3/2016 | Rajeev et al. |
| 9,403,865 B2 | 8/2016 | Cedillo et al. |
| 9,994,855 B2 | 6/2018 | Prakash et al. |
| 2001/0053519 A1 | 12/2001 | Fodor et al. |
| 2003/0077829 A1 | 4/2003 | MacLachlan |
| 2003/0119724 A1 | 6/2003 | Ts'o et al. |
| 2003/0158403 A1 | 8/2003 | Manoharan et al. |
| 2003/0170249 A1 | 9/2003 | Hakomori et al. |
| 2003/0175906 A1 | 9/2003 | Manoharan et al. |
| 2003/0228597 A1 | 12/2003 | Cowsert et al. |
| 2004/0171570 A1 | 9/2004 | Allerson et al. |
| 2004/0242516 A1 | 12/2004 | Crooke et al. |
| 2004/0259086 A1 | 12/2004 | Schlegel et al. |
| 2005/0009088 A1 | 1/2005 | Crooke et al. |
| 2005/0112118 A1 | 5/2005 | Cimbora et al. |
| 2005/0130923 A1 | 6/2005 | Bhat et al. |
| 2005/0164235 A1 | 7/2005 | Manoharan et al. |
| 2005/0244869 A1 | 11/2005 | Brown-Driver et al. |
| 2006/0148740 A1 | 7/2006 | Platenburg |
| 2006/0183886 A1 | 8/2006 | Tso et al. |
| 2006/0264395 A1 | 11/2006 | Crooke et al. |
| 2007/0031844 A1 | 2/2007 | Khvorova et al. |
| 2007/0287831 A1 | 12/2007 | Seth et al. |
| 2008/0039618 A1 | 2/2008 | Allerson et al. |
| 2008/0108801 A1 | 5/2008 | Manoharan et al. |
| 2008/0206869 A1 | 8/2008 | Smith et al. |
| 2008/0281041 A1 | 11/2008 | Rozema et al. |
| 2008/0281044 A1 | 11/2008 | Manoharan et al. |
| 2009/0012281 A1 | 1/2009 | Swayze et al. |
| 2009/0203132 A1 | 8/2009 | Swayze et al. |
| 2009/0203135 A1 | 8/2009 | Forst et al. |
| 2009/0286973 A1 | 11/2009 | Manoharan et al. |
| 2009/0306180 A1 | 12/2009 | Bhanot et al. |
| 2009/0326040 A1 | 12/2009 | Geary et al. |
| 2010/0190837 A1 | 7/2010 | Migawa et al. |
| 2010/0197762 A1 | 8/2010 | Swayze et al. |
| 2010/0240730 A1 | 9/2010 | Beigelman et al. |
| 2010/0331390 A1 | 12/2010 | Crooke et al. |
| 2011/0039910 A1 | 2/2011 | Crooke et al. |
| 2011/0077386 A1 | 3/2011 | Lee et al. |
| 2011/0097264 A1 | 4/2011 | Wang et al. |
| 2011/0097265 A1 | 4/2011 | Wang et al. |
| 2011/0123520 A1 | 5/2011 | Manoharan et al. |
| 2011/0124853 A1 | 5/2011 | Chen et al. |
| 2011/0201798 A1 | 8/2011 | Manoharan et al. |
| 2011/0207799 A1 | 8/2011 | Rozema et al. |
| 2011/0269814 A1 | 11/2011 | Manoharan et al. |
| 2012/0035115 A1 | 2/2012 | Manoharan et al. |
| 2012/0071641 A1 | 3/2012 | Manoharan et al. |
| 2012/0095075 A1 | 4/2012 | Manoharan et al. |
| 2012/0101148 A1 | 4/2012 | Aking et al. |
| 2012/0122958 A1 | 5/2012 | Dawson et al. |
| 2012/0128760 A1 | 5/2012 | Manoharan et al. |
| 2012/0136042 A1 | 5/2012 | Manoharan et al. |
| 2012/0157509 A1 | 6/2012 | Hadwiger et al. |
| 2012/0165393 A1 | 6/2012 | Rozema et al. |
| 2012/0183602 A1 | 7/2012 | Chen et al. |
| 2012/0225927 A1 | 9/2012 | Sah et al. |
| 2012/0230938 A1 | 9/2012 | Rozema et al. |
| 2013/0004427 A1 | 1/2013 | El-Sayed et al. |
| 2013/0035366 A1 | 2/2013 | Swayze et al. |
| 2013/0053431 A1 | 2/2013 | Tachas et al. |
| 2013/0109817 A1 | 5/2013 | Yurkovetskiy et al. |
| 2013/0121954 A1 | 5/2013 | Wakefield et al. |
| 2013/0130378 A1 | 5/2013 | Manoharan et al. |
| 2013/0178512 A1 | 7/2013 | Manoharan et al. |
| 2013/0236968 A1 | 9/2013 | Manoharan et al. |
| 2013/0317085 A1 | 11/2013 | Crooke et al. |
| 2014/0107330 A1 | 4/2014 | Freier et al. |
| 2015/0018540 A1 | 1/2015 | Prakash et al. |
| 2015/0184153 A1 | 7/2015 | Freier et al. |
| 2015/0191727 A1 | 7/2015 | Migawa et al. |
| 2015/0218205 A1 | 8/2015 | Cedillo et al. |
| 2015/0267195 A1 | 9/2015 | Seth et al. |
| 2015/0275212 A1 | 10/2015 | Albaek et al. |
| 2015/0368288 A1 | 12/2015 | Cedillo et al. |
| 2016/0122761 A1 | 5/2016 | Prakash et al. |

FOREIGN PATENT DOCUMENTS

| | | |
|---|---|---|
| WO | WO 1995/019433 | 7/1995 |
| WO | WO 1997/020563 | 6/1997 |
| WO | WO 1997/046098 | 12/1997 |
| WO | WO 1998/013381 | 4/1998 |
| WO | WO 1999/014226 | 3/1999 |
| WO | WO 2000/014048 | 3/2000 |
| WO | WO 2000/076554 | 12/2000 |
| WO | WO 2001/053528 | 7/2001 |
| WO | WO 2002/043771 | 6/2002 |
| WO | WO 2002/092772 | 11/2002 |
| WO | WO 2003/010284 | 2/2003 |
| WO | WO 2004/024757 | 3/2004 |
| WO | WO 2004/044181 | 5/2004 |
| WO | WO 2004/063208 | 7/2004 |
| WO | WO 2004/071407 | 8/2004 |
| WO | WO 2004/093783 | 11/2004 |
| WO | WO 2004/096016 | 11/2004 |
| WO | WO 2004/096996 | 11/2004 |
| WO | WO 2004/101619 | 11/2004 |
| WO | WO 2004/106356 | 12/2004 |
| WO | WO 2005/000201 | 1/2005 |
| WO | WO 2005/005599 | 1/2005 |
| WO | WO 2005/028628 | 1/2005 |
| WO | WO 2005/021570 | 3/2005 |
| WO | WO 2005/121371 | 6/2005 |
| WO | WO 2005/071080 | 8/2005 |
| WO | WO 2005/083124 | 9/2005 |
| WO | WO 2005/097155 | 10/2005 |
| WO | WO 2006/031461 | 3/2006 |
| WO | WO 2006/044531 | 4/2006 |
| WO | WO 2007/035759 | 3/2007 |
| WO | WO 2007/035771 | 3/2007 |
| WO | WO 2007/090071 | 8/2007 |
| WO | WO 2007/131237 | 11/2007 |
| WO | WO 2007/134014 | 11/2007 |
| WO | WO 2007/134181 | 11/2007 |
| WO | WO 2007/136988 | 11/2007 |
| WO | WO 2007/143317 | 12/2007 |
| WO | WO 2008/066776 | 6/2008 |
| WO | WO 2008/098788 | 8/2008 |
| WO | WO 2008/101157 | 8/2008 |
| WO | WO 2008/150729 | 12/2008 |
| WO | WO 2008/154401 | 12/2008 |
| WO | WO 2009/003009 | 12/2008 |
| WO | WO 2009/006478 | 1/2009 |
| WO | WO 2009/046141 | 4/2009 |
| WO | WO 2009/061851 | 5/2009 |
| WO | WO 2009/073809 | 6/2009 |
| WO | WO 2009/082607 | 7/2009 |
| WO | WO 2009/126933 | 10/2009 |
| WO | WO 2009/134487 | 11/2009 |
| WO | WO 2009/143369 | 11/2009 |
| WO | WO 2009/148605 | 12/2009 |

(56) References Cited

FOREIGN PATENT DOCUMENTS

| | | |
|---|---|---|
| WO | WO 2010/017509 | 2/2010 |
| WO | WO 2010/036698 | 4/2010 |
| WO | WO 2010/045509 | 4/2010 |
| WO | WO 2010/048549 | 4/2010 |
| WO | WO 2010/048585 | 4/2010 |
| WO | WO 2010/054406 | 5/2010 |
| WO | WO 2010/077578 | 7/2010 |
| WO | WO 2010/083615 | 7/2010 |
| WO | WO 2010/088537 | 8/2010 |
| WO | WO 2010/101951 | 9/2010 |
| WO | WO 2010/103204 | 9/2010 |
| WO | WO 2010/121074 | 10/2010 |
| WO | WO 2010/129709 | 11/2010 |
| WO | WO 2010/144740 | 12/2010 |
| WO | WO 2010/148013 | 12/2010 |
| WO | WO 2011/005860 | 1/2011 |
| WO | WO 2011/005861 | 1/2011 |
| WO | WO 2011/038356 | 3/2011 |
| WO | WO 2011/047312 | 4/2011 |
| WO | WO 2011/100131 | 8/2011 |
| WO | WO 2011/115818 | 9/2011 |
| WO | WO 2011/120053 | 9/2011 |
| WO | WO 2011/133871 | 10/2011 |
| WO | WO 2011/139702 | 10/2011 |
| WO | WO 2011/139917 | 11/2011 |
| WO | WO 2011/163121 | 12/2011 |
| WO | WO 2012/037254 | 3/2012 |
| WO | WO 2012/068187 | 5/2012 |
| WO | WO 2012/083046 | 6/2012 |
| WO | WO 2012/083185 | 6/2012 |
| WO | WO 2012/089352 | 7/2012 |
| WO | WO 2012/089602 | 7/2012 |
| WO | WO 2012/135736 | 10/2012 |
| WO | WO 2012/142458 | 10/2012 |
| WO | WO 2012/145674 | 10/2012 |
| WO | WO 2012/145697 | 10/2012 |
| WO | WO 2012/149495 | 11/2012 |
| WO | WO 2012/174154 | 12/2012 |
| WO | WO 2012/177947 | 12/2012 |
| WO | WO 2013/033230 | 3/2013 |
| WO | WO 2013/043817 | 3/2013 |
| WO | WO 2013/075035 | 5/2013 |
| WO | WO 2013/119979 | 8/2013 |
| WO | WO 2013/142514 | 9/2013 |
| WO | WO 2013/165816 | 11/2013 |
| WO | WO 2013/166121 | 11/2013 |
| WO | WO 2013/173789 | 11/2013 |
| WO | WO 2013/177468 | 11/2013 |
| WO | WO 2014/025805 | 2/2014 |
| WO | WO 2014/076195 | 5/2014 |
| WO | WO 2014/076196 | 5/2014 |
| WO | WO 2014/118267 | 8/2014 |
| WO | WO 2014/118272 | 8/2014 |
| WO | WO 2014/120861 | 8/2014 |
| WO | WO 2014/179620 | 11/2014 |
| WO | WO 2014/179625 | 11/2014 |
| WO | WO 2014/179626 | 11/2014 |
| WO | WO 2014/179627 | 11/2014 |
| WO | WO 2014/179629 | 11/2014 |
| WO | WO 2014/207232 | 12/2014 |
| WO | WO 2015/006740 | 1/2015 |
| WO | WO 2016/055601 | 4/2016 |
| WO | WO 2017/004261 | 1/2017 |

OTHER PUBLICATIONS

Agrawal et al., "Protecting Groups in Oligonucleotide Synthesis" Protocols for Oligonucleotide Conjugates, Humana Press; New Jersey (1994) 26: 1-71.

Akinc et al., "Targeted Delivery of RNAi Therapeutics with Endogenous and Exogenous Ligand-Based Mechanisms" Molecular Therapy (2010) 18(7): 1357-1364.

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Andre et al., "Determination of modulation of ligand properties of synthetic complex-type biantennary N-glycans by introduction of bisecting GlcNAc in silico, in vitro and in vivo" Eur. J. Biochem. (2004) 271: 118-134.

Asseline et al., "Modification of the 5' Terminus of Oligodeoxyribonucleotides for Conjugation with Ligands" in Current Protocols in Nucleic Acid Chemistry, 2001, Supplement 5, Chapter 4: Unit 4.9 (4.9.1-4.9.28); John Wiley & Sons.

Atsma et al., "Partial characterization of low density lipoprotein preparations isolated from fresh and frozen plasma after radiolabeling by seven different methods." J Lipid Res. (1991) 32(1): 173-181.

Barany et al., "A New Amino Protecting Group Removable by Reduction. Chemistry of the Dithiasuccinoyl (Dts) Function" J Am Chem Soc (1977) 99: 7363-7365.

Barany et al., "Kinetics and mechanism of the thiolytic removal of the dithiasuccinoyl (Dts) amino protecting group" J Am Chem Soc (1980) 102: 3084-3095.

Beaucage et al., "The functionalization of oligonucleotides via phosphoramidate derivatives" Tetrahedron (1993) 49(10): 1925-1963.

Beaucage et al., "Advances in the Synthesis of Oligonucleotides by the Phosphoramidite Approach" Tetrahedron (1992) 48: 2223-2311.

Beaucage et al., "The synthesis of specific ribonucleotides and unrelated phosphorylated biomolecules by the phosphoramidite method" Tetrahedron (1993) 49: 10441-10488.

Bergeron et al., "Subtilase-like pro-protein convertases: from molecular specificity to therapeutic applications." J Mol Endocrinol. (2000) 24(1): 1-22.

Biessen et al., "Novel hepatotrophic prodrugs of the antiviral nucleoside 9-(2-phosphonylmethoxyethyl)adenine with improved pharmacokinetics and antiviral activity" FASEB J. (2000) 14: 1784-1792.

Biessen et al., "Synthesis of Cluster Galactosides with High Affinity for the Hepatic Asialoglycoprotein Receptor" J. Med. Chem. (1995) 38:1538-1546.

Biessen et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852.

Bock et al., "Glycosylation Reactions With Di-O-Acetyl-2,6-Dibromo-2,6-Dideoxy-Alpha-D-Mannopyranosyl Bromide: A Simple Synthesis of Methyl 2,6-Dideoxy-Barabino-Hexopyranoside" Acta Chemica Scandinavica (1998) B42: 640-645.

Braasch et al., "Locked nucleic acid (LNA): fine-tuning the recognition of DNA and RNA" Chem. Biol. (2001) 8:1-7.

Braasch et al., "Novel Antisense and Peptide Nucleic Acid Strategies for Controlling Gene Expression" Biochemistry (2002) 41(14): 4503-4510.

Branch et al., "A good antisense molecule is hard to find," TIBS (1998) 23:45-50.

Branda et al., "Amplification of antibody production by phosphorothioate oligodeoxynucleotides" J Lab Clin Med. (1996) 128(3): 329-338.

Brubaker et al., "Structure-Function of the Glucagon Receptor Family of G Protein-Coupled Receptors: The Glucagon, GIP, GLP-1, and GLP-2 Receptors" Receptors and Channels (2002) 8: 179-188.

Chen et al., "Strand-specific 5'-O-methylation of siRNA duplexes controls guide strand selection and targeting specificity" RNA. (2008) 14:263-74.

Chiang et al., "Antisense Oligonucleotides Inhibit Intercellular Adhesion Molecule 1 Expression by Two Distinct Mechanisms" J. Biol. Chem. (1991) 266:18162-18171.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

(56) References Cited

OTHER PUBLICATIONS

Coltart et al., "Principles of Mucin Architecture: Structural Studies on Synthetic Glycopeptides Bearing Clustered Mono-, Di-, Tri-, and Hexasaccharide Glycodomains" J. Am. Chem. Soc. (2002) 124: 9833-9844.
Connolly et al., "Binding and Endocytosis of Cluster Glycosides by Rabbit Hepatocytes" J Biol Chem (1982) 257: 939-945.
Costa et al., "Amyloid fibril protein related to prealbumin in familial amyloidotic polyneuropathy" PNAS (1978) 75(9): 4499-4503.
Crew et al., "Eukaryotic initiation factor-4E in superficial and muscle invasive bladder cancer and its correlation with vascular endothelial growth factor expression and tumour progression" Br J Cancer (2000) 82(1): 161-166.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Crooke et al., "Pharmacological Properties of 2'-O-Methoxyethyl Modified Oligonucleotides" in Antisense a Drug Technology, Chapter 10, pp. 273-303, Crooke, S.T., ed., 2008.
Crooke et al., "Toxicologic Properties of 2-O-Methoxyethyl Chimeric Antisense Inhibitors in Animals and Man" in Antisense a Drug Technology, Chapter 12, pp. 342-351, Crooke, S.T., ed., 2008.
Crooke, ST., et al., "Antisense Drug Technology" Second Edition, CRC Press (2008) Chapters 1-28.
Czech et al. "RNAi-based therapeutic strategies for metabolic disease" Nature Reviews Endocrinology (2011) 7: 473-484.
Davidson et al., "Apolipoprotein B: mRNA Editing, Lipoprotein Assembly, and Presecretory Degradation" Annu. Rev. Nutr. (2000) 20: 169-193.
De Benedetti et al., "Overexpression of eukaryotic protein synthesis initiation factor 4E in HeLa cells results in aberrant growth and morphology" PNAS (1990) 87: 8212-8216.
Dellinger et al., "Solid-Phase Chemical Synthesis of Phosphonoacetate and Thiophosphonoacetate Oligodeoxynucleotides" J. Am .Chem. Soc. (2003) 125: 940-950.
Dickson et al., "Rat Choroid Plexus Specializes in the Synthesis and the Secretion of Transthyretin" J Biol Chem (1986) 261(8): 3475-3478.
Dubuc et al., "Statins upregulate PCSK9, the gene encoding the proprotein convertase neural apoptosis-regulated convertase-1 implicated in familial hypercholesterolemia." Arterioscler Thromb Vasc Biol. (2004) 24(8): 1454-1459.
Duff et al., "Intrabody Tissue-Specific Delivery of Antisense Conjugates in Animals: Ligand-Linker-Antisense Oligomer Conjugates" Methods in Enzymology (1999) 313: 297-321.
Dupouy et al., "Watson-Crick Base-Pairing Properties of Nucleic Acid Analogues with Stereocontrolled a and b Torsion Angles (a,b-D-CNAs)" Angew. Chem. Int. Ed. (2006) 45: 3623-3627.
Egli, et al., "Synthesis, improved antisense activity and structural rationale for the divergent RNA affinities of 3'-fluoro hexitol nucleic acid (FHNA and Ara-FHNA) modified oligonucleotides." J Am Chem (2011) 133(41):16642-16649.
Elayadi et al., "Application of PNA and LNA oligomers to chemotherapy" Curr. Opinion Invens. Drugs (2001) 2:558-561.
Elchebly et al., "Increased Insulin Sensitivity and Obesity Resistance in Mice Lacking the Protein Tyrosine Phosphatase-1B Gene" Science (1999) 283: 1544-1548.
Encio et al., "The Genomic Structure of the Human Glucocorticoid Receptor" J Biol Chem (1991) 266(11): 7182-7188.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Fried et al., "HBeAg and hepatitis B virus DNA as outcome predictors during therapy with peginterferon alfa-2a for HBeAg-positive chronic hepatitis B." Hepatology (2008) 47(2): 428-434.

Frieden et al., "Expanding the design horizon of antisense oligonucleotides with alpha-L-LNA" Nucleic Acids Research (2003) 31(21):6365-6372.
Fukada et al., "Two signals are necessary for cell proliferation induced by a cytokine receptor gp130: involvement of STAT3 in anti-apoptosis." Immunity (1996) 5(5): 449-460.
Gait et al., "Applications of chemically synthesized RNA" Protein Interactions, Smith Ed. (1998) 1-36.
Gallo et al., "2'-C-Methyluridine phosphoramidite: a new building block for the preparation for RNA analogues carrying the 2'-hydroxyl group" Tetrahedron (2001) 57: 5707-5713.
Ganem et al., "Hepatitis B Virus Infection—Natural History and Clinical Consequences" N Engl J Med. (2004) 350: 1118-1129.
Gautschi et al., "Activity of a novel bcl-2/bcl-xLbispecific antisense oligonucleotide against tumors of diverse histologic origins" J. Natl. Cancer Inst. (2001) 93:463-471.
Geary et al., "Pharmacokinetic Properties of 2'-O-(2-Methoxyethyl)-Modified Oligonucleotide Analogs in Rats" The Journal of Pharmacology and Experimental Therapeutics (2001) 296:890-897.
Geary et al.,"Effect of Dose and Plasma Concentration on Liver Uptake and Pharmacologic Activity of a 2'-Methoxyethyl Modified Chimeric Antisense Oligonucleotide Targeting PTEN." Biochem. Pharmacol. (2009) 78(3): 284-91.
Gehring et al., "Assignment of the human gene for the glucocorticoid receptor to chromosme 5" PNAS (1985) 82: 3751-3755.
Gensberg et al., "Subtilisin-related serine proteases in the mammalian constitutive secretory pathway." Semin Cell Dev Biol. (1998) 9(1): 11-17.
Giguere et al., "Functional Domains of the Human Glucocorticoid Receptor" Cell (1986) 46: 645-652.
Gough et al., "Mitochondrial STAT3 supports Ras-dependent oncogenic transformation." Science (2009) 324(5935): 1713-1716.
Graff et al., "Translational control and metastatic progression: Enhanced activity of the mRNA cap-binding protein eIF-4E selectively enhances translation of metastasis-related mRNAs" Clin. Exp. Metastasis (2003) 20: 265-273.
Gravert et al., "Organic Synthesis on Soluble Polymer Supports: Liquid-Phase Methodologies" Chem Rev. (1997) 97: 489-510.
Hansen et al., "Glucagon Receptor mRNA Distribution in Rat Tissues" Peptides (1995) 16(6): 1163-1166.
Haydon et al., "Progression of eIF4E Gene Amplification and Overexpression in Benign and Malignant Tumors of the Head and Neck" Cancer (2000) 88(12): 2803-2810.
Henry et al., "Drug properties of second-generation antisense oligonucleotides: how do they measure up to their predecessors?" Curr Opin Investig Drugs (2001) 2: 1444-1449.
Hoffman et al., "'Brain-type' N-glycosylation of asialo-transferrin from human cerebrospinal fluid" FEBS Letters (1995) 359: 164-168.
Hollenberg et al., "Primary structure and expression of a functional human glucocorticoid receptor cDNA" Nature (1985) 318: 635-641.
Horn et al., "Chemical synthesis and characterization of branched oligodeoxyribonucleotides (bDNA) for use as signal amplifiers in nucleic acid quantification assays." Nucleic Acids Research (1997) 25: 4842-4849.
Horton et al., "Combined analysis of oligonucleotide microarray data from transgenic and knockout mice identifies direct SREBP target genes" PNAS (2003) 100(21): 12027-12032.
Jain et al., "Repression of Stat3 activity by activation of mitogen-activated protein kinase (MAPK)." Oncogene (1998) 17(24): 3157-3167.
Jayaprakash et al., "Non-Nucleoside Building Blocks for Copper-Assisted and Copper-Free Click Chemistry for the Efficient Synthesis of RNA Conjugates" Organic Letters (2010) 12(23): 5410-5413.
Jervis et al., "New CD1d agonists: synthesis and biological activity of 6"-triazole-substituted α-galactosyl ceramides" Bioorg Med Chem Lett. (2012) 22(13):4348-52.
Jiang et al., "Glucagon and regulation of glucose metabolism" Am J Physiol Endocrinol Metab. (2003) 284: E671-E678.
Jiang et al., "The Design and Synthesis of Highly Branched and Spherically Symmetric Fluorinated Oils and Amphiles." Tetrahedron (2007) 63(19): 3982-3988.

(56) References Cited

OTHER PUBLICATIONS

Jin et al., "Use of α-N,N-bis[Carboxymethyl]lysine-Modified Peroxidase in Immunoassays" Analytical Biochemistry (1995) 229: 54-60.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Kanasty et al., "Delivery Materials for siRNA Therapeutics" Nature Materials (2013) 12: 967-977.
Kassim et al., "Gene therapy for dyslipidemia: a review of gene replacement and gene inhibition strategies" Clinical Lipidology (2010) 5(6): 793-809.
Kato et al., "N-acetylgalactosamine incorporation into a peptide containing consecutive threonine residues by UDP-N-acetyl-D-galactosaminide:polypeptide N-acetylgalactosaminyltransferases" Glyobiology (2001) 11: 821-829.
Kerekatte et al., "The proto-oncogene/translation factor eIF4E: a survey of its expression in breast carcinomas." Int J Cancer (1995) 64: 27-31.
Khorev et al., "Trivalent, Gal/GalNAc-containing ligands designed for the asialoglycoprotein receptor" Bioorganic & Medicinal Chemistry (2008) 16: 5216-5231.
Kim et al., "Oligomeric Glycopeptidomimetics Bearing the Cancer Related TN-Antigen" Tetrahedron Letters (1997) 38(20): 3487-3490.
Kim et al., "Synthesis of Novel Phosphoramidite Building Blocks from Pentaerythritol" Synlett (2003) 12: 1838-1840.
Klaman et al., "Increased Energy Expenditure, Decreased Adiposity, and Tissue-Specific Insulin Sensitivity in Protein-Tyrosine Phosphatase 1B-Deficient Mice" Mol. Cell. Biol. (2000) 20(15): 5479-5489.
Koller et al., "Mechanisms of single-stranded phosphorothioate modified antisense oligonucleotide accumulation in hepatocytes." Nucleic Acids Res. (2011) 39(11): 4795-4807.
Kornilova et al., "Development of a fluorescence polarization binding assay for asialoglycoprotein receptor" Analytical Biochemistry (2012) 425: 43-46.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Kroschwitz, "Polynucleotides" Concise Encyclopedia of Polymer Science and Engineering (1990) John Wiley & Sons, NY pp. 858-859.
Kumar et al., "The first analogues of LNA (locked nucleic acids): phosphorothioate-LNA and 2'-thio-LNA" Bioorg Med Chem Lett. (1998) 8:2219-2222.
Kurosawa et al., "Selective silencing of a mutant transthyretin allele by small interfering RNAs" Biochemical and Biophysical Research Communications (2005) 337 (3): 1012-1018.
Lazaris-Karatzas et al., "Malignant transformation by a eukaryotic initiation factor subunit that binds to mRNA 5' cap" Nature (1990) 345: 544-547.
Lee et al., "Synthesis of some cluster glycosides suitable for attachment to proteins or solid matrices" Carbohydrate Research (1978) 67: 509-514.
Lee et al., "Facile Synthesis of a High-Affinity Ligand for Mammalian Hepatic Lectin Containing Three Terminal N-Acetylgalactosamine Residues" Bioconjugate Chem. (1997) 8: 762-765.
Lee et al., "New and more efficient multivalent glyco-ligands for asialoglycoprotein receptor of mammalian hepatocytes" Bioorganic & Medicinal Chemistry (2011) 19:2494-2500.
Lee et al., "Preparation of Cluster Glycosides of Nacetylgalactosamine That Have Subnanomolar Binding Constants Towards the Mammalian Hepatic Gal/GalNAc-specific Receptor" Glycoconjugate J. (1987) 4: 317-328.
Lee et al., "Synthesis of Peptide-Based Trivalent Scaffold for Preparation of Cluster Glycosides" Methods in Enzymology (2003) 362: 38-43.

Lee et al., "New synthetic cluster ligands for galactose/N-acetylgalactosamine-specific lectin of mammalian liver" Biochem (1984) 23: 4255-4261.
Lee et al., "Protein microarrays to study carbohydrate-recognition events" Bioorg Med Chem Lett (2006) 16(19): 5132-5135.
Lee et al., "Synthesis of multivalent neoglyconjugates of MUC1 by the conjugation of carbohydrate-centered, triazole-linked glycoclusters to MUC1 peptides using click chemistry," J Org Chem (2012) 77: 7564-7571.
Lee et al., "Antisense Technology: An Emerging Platform for Cardiovascular Disease Therapeutics" J of Cardiovasc Trans Res (2013) 6: 969-980.
Leren, "Mutations in the PCSK9 gene in Norwegian subjects with autosomal dominant hypercholesterolemia." Clin. Genet. (2004) 65(5): 419-422.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann et al., "DNA Analogues: From Supramolecular Principles to Biological Properties" Bioorganic & Medicinal Chemistry (2002) 10:841-854.
Liang et al., "Hepatitis B e Antigen—The Dangerous Endgame of Hepatitis B" N Engl J Med. (2002) 347: 208-210.
Lima et al., "Single-stranded siRNAs activate RNAi in animals" Cell (2012) 150:883-94.
Link, "Pharmacological regulation of hepatic glucose production" Curr Opin Investig Drugs (2003) 4: 421-429.
Machida et al., "Postmortem findings in a patient with cerebral amyloid angiopathy actively treated with corticosteroid" Amyloid (2012) 19: 47-49.
Maher et al., "Comparative hybrid arrest by tandem antisense oligodeoxyribonucleotides or oligodeoxyribonucleoside methylpbosphonates in a cell-free system" Nucl. Acid. Res. (1988) 16(8):3341-3358.
Maier et al., "Synthesis of Antisense Oligonucleotides Conjugated to a Multivalent Carbohydrate Cluster for Cellular Targeting" Bioconjugate Chem. (2003) 14: 18-29.
Maierhofer et al., "Probing multivalent carbohydrate-lectin interactions by an enzyme-linked lectin assay employing covalently immobilized carbohydrates" Bioorganic & Medicinal Chemistry (2007) 15: 7661-7676.
Makino et al., "Intravenous Injection with Antisense Oligodeoxynucleotides Against Angiotensinogen Decreases Blood Pressure in Spontaneously Hypertensive RatS" Hypertension (1998) 31: 1166-1170.
Manoharan et al., "Chemical Modifications to Improve Uptake and Bioavailability of Antisense Oligonucleotides" Ann. N.Y. Acad. Sci. (1992) 660: 306-309.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids" Tetrahedron Lett. (1995) 36(21):3651-3654.
Manoharan et al., "N-(2-Cyanoethoxycarbonyloxy)succinimide: A New Reagent for Protection of Amino Groups in Oligonucleotides" J. Org. Chem. (1999) 64: 6468-6472.
Manoharan et al., "Oligonucleotide Conjugates: Alteration of the Pharmacokinetic Properties of Antisense Agents" Nucleosides & Nucleotides (1995) 14(3-5):969-973.
Manoharan, "Oligonucleotide Conjugates as Potential Antisense Drugs with Improved Uptake, Biodistribution, Targeted Delivery, and Mechanism of Action" Antisense & Nucleic Acid Drug Development (2002) 12: 103-128.
Marcaurelle et al., "Synthesis of Oxime-Linked Mucin Mimics Containing the Tumor-Related TN and Sialyl TN Antigens" Organic Letters (2001) 3(23): 3691-3694.
Maxwell et al., "Novel putative SREBP and LXR target genes identified by microarray analysis in liver of cholesterol-fed mice." J. Lipid Res. (2003) 44(11): 2109-2119.

(56) References Cited

OTHER PUBLICATIONS

Merwin et al., "Targeted delivery of DNA using YEE(GalNAcAH)3, a synthetic glycopeptide ligand for the asialoglycoprotein receptor." Bioconjug Chem (1994) 5(6): 612-620.
Mishra et al., "Improved leishmanicidal effect of phosphorotioate antisense oligonucleotides by LDL-mediated delivery" Biochim. Biophys. Acta (1995) 1264:229-237.
Miura et al., "Fluorometric determination of total mRNA with oligo(dT) immobilized on microtiter plates" Clin. Chem. (1996) 42:1758-1764.
Moucari et al., "Early serum HBsAg drop: a strong predictor of sustained virological response to pegylated interferon alfa-2a in HBeAg-negative patients." Hepatology (2009) 49(4): 1151-1157.
Neel et al., "Protein tyrosine phosphatases in signal transduction." Curr Opin Cell Biol. (1997) 9(2): 193-204.
New England Biolabs 1998/99 Catalog (cover page and pp. 121 and 284).
Nishimura et al., "Synthetic Glycoconjugates. 4. Use of .omega.-(Acrylamido)alkyl Glycosides for the Preparation of Cluster Glycopolymers" Am. Chem. Soc. (1994) 27(18): 4876-4880.
Oberhauser et al., "Effective incorporation of 2'-O-methyl-oligoribonucleotides into liposomes and enhanced cell association through modifiations with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Palha, "Transthyretin as a Thyroid Hormone Carrier: Function Revisited" Clin Chem Lab Med (2002) 40(12): 1292-1300.
Park et al., "The asialoglycoprotein receptor clears glycoconjugates terminating with sialic acid a2,6GalNAc" PNAS (2005) 102(47): 17125-17129.
Pavia et al., "Synthetic TN glycopeptide related to human glycophorin AM. High-field proton and carbon-13 nuclear magnetic resonance study." Int J Pep Protein Res (1983) 22: 539-548.
Petrova et al., "Carrier-free cellular uptake and the gene-silencing activity of the lipophilic siRNAs is strongly affected by the length of the linker between siRNA and lipophilic group" Nucleic Acids Research (2012) 40(5): 2330-2344.
Prakash et al., "Identification of metabolically stable 5'-phosphate analogs that support single-stranded siRNA activity" Nucleic Acids Res. (2015) 43:2993-3011.
Pujol et al., "A Sulfur Tripod Glycoconjugate that Releases a High-Affinity Copper Chelator in Hepatocytes" Angew. Chem. Int. Ed. (2012) 51: 7445-7448.
Quesada et al., "Physiology of the pancreatic a-cell and glucagon secretion: role in glucose homeostasis and diabetes" J Endocrinol. (2008) 199: 5-19.
Rajeev, "Conjugation Strategies for In Vitro siRNA Delivery" 8th Annual Meeting of the Oligonucleotide Therapeutics Society (2012).
Rajur et al., "Covalent Protein-Oligonucleotide Conjugates for Efficient Delivery of Antisense Molecules" Bioconjugate Chem. (1997) 8: 935-940.
Raouane et al., "Synthesis, Characterization, and in Vivo Delivery of siRNA-Squalene Nanoparticles Targeting Fusion Oncogene in Papillary Thyroid Carcinoma" J. Med. Chem. (2011) 54: 4067-4076.
Rensen et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808.
Rensen et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584.
Rensen et al., "Stimulation of Liver-Directed Cholesterol Flux in Mice by Novel N-Acetylgalactosamine—Terminated Glycolipids With High Affinity for the Asialoglycoprotein Receptor" Arterioscler Thromb Vasc Biol (2006) 26: 169-175.
Reynolds et al., "Rational siRNA design for RNA interference" Nature Biotechnology (2004) 22(3):326-330.
Rosenwald et al., "Upregulation of protein synthesis initiation factor eIF-4E is an early event during colon carcinogenesis" Oncogene (1999) 18: 2507-2517.
Rosenwald et al., "Growth factor-independent expression of the gene encoding eukaryotic translation initiation factor 4E in transformed cell lines" Cancer Lett. (1995) 98: 77-82.
Rossenberg et al., "Stable polyplexes based on arginine-containing oligopeptides for in vivo gene delivery" Gene Therapy (2004) 11: 457-464.
Rouchaud et al., "A New and Efficient Synthesis of Derivatives of Octahydro-4H-pyrrolo[1,2-c]pyrido[1',2'-a]imidazole" Eur. J. Org. Chem. (2011) 12: 2346-2353.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sakaki et al., "Human Transthyretin (Prealbumin) Gene and Molecular Genetics of Familial Amyloidotic Polyneruopathy" Mol Biol Med. (1989) 6: 161-168.
Sambrook et al., "Molecular Cloning, a laboratory manual" 2nd edition, Cold Spring Harbor Laboratory Press (1989).
Sanghvi et al., "Heterocyclic Base Modifications in Nucleic Acids and Their Applications in Antisense Oligonucleotides" Antisense Research and Applications (1993) pp. 273-288.
Sanghvi, Chapter 15, Antisense Research and Applications, Crooke and Lebleu ed., CRC Press (1993).
Sanghvi et al., "Synthesis of Nonionic Oligonucleotide Analogues" Carbohydrate Modifications in Antisense Research, ACS Symposium: (1994) Chapters 3 & 4.
Sanghvi et al., "Carbohydrate Modifications in Antisense Research" American Chemical Society, Washington D.C. (1994).
Saraiva et al., "Amyloid Fibril Protein in Familial Amyloidotic Polyneuropathy, Portuguese Type" J Clin Invest. (1984) 74: 104-119.
Sato et al., "Glycoinsulins: Dendritic Sialyloligosaccharide-Displaying Insulins Showing a Prolonged Blood-Sugar-Lowering Activity" J. Am. Chem. Soc. (2004) 126: 14013-14022.
Scaringe et al., "RNA Oligonucleotide Synthesis via 5'-Silyl-2'-Orthoester Chemistry" Methods (2001) 23: 206-217.
Seeger et al., "Hepatitis B virus biology" Microbiol Mol Biol Rev. (2000) 64(1): 51-68.
Seth et al., "Synthesis and biophysical characterization of R-6'-Me-α-L-LNA modified oligonucleotides." Bioorg. Med. Chem. (2011) 21(4): 1122-1125.
Seth et al., "Synthesis and Biophysical Evaluation of 2',4'-Constrained 2'O-Methoxyethyl and 2',4'-Constrained 2'O-Ethyl Nucleic Acid Analogues" J Org Chem. (2010) 75(5): 1569-1581.
Seth et al., "Design, Synthesis And Evaluation Of Constrained Methoxyethyl (cMOE) and Constrained Ethyl (cEt) Nucleoside Analogs" Nucleic Acids Symposium Series (2008) 52(1): 553-554.
Seth et al., "Short Antisense Oligonucleotides with Novel 2'-4' Conformationaly Restricted Nucleoside Analogues Show Improved Potency Without Increased Toxicity in Animals." J Med Chem (2009) 52:10-13.
Shchepinov et al., "Oligonucleotide dendrimers: synthesis and use as polylabelled DNA probes." Nucleic Acids Research (1997) 25(22): 4447-4454.
Shchepinov et al., "Oligonucleotide dendrimers: stable nano-structures" Nucleic Acids Research (1999) 27(15): 3035-3041.
Shea et al., "Synthesis, hybridization properties and antiviral activity of lipid-oligodeoxynucleotide conjugates" Nucl. Acids Res. (1990) 18(13):3777-3783.
Shioji et al., "Genetic variants in PCSK9 affect the cholesterol level in Japanese." J. Hum. Genet. (2004) 49: 109-114.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Sliedregt et al., "Design and Synthesis of Novel Amphiphilic Dendritic Galactosides for Selective Targeting of Liposomes to the Hepatic Asialoglycoprotein Receptor" J. Med. Chem. (1999) 42:609-618.

(56) References Cited

OTHER PUBLICATIONS

Sofia et al., "Discovery of a beta-d-2'-deoxy-2'-alpha-fluoro-2'-beta-C-methyluridine Nucleotide Prodrug (PSA-7977) For the Treatment of Hepatitis C virus" J. Med. Chem. (2010) 53(19): 7202-7218.
Sousa et al., "Neurodegeneration in familial amyloid polyneuropathy: from pathology to molecular signaling" Prog Neurobiol (2003) 71: 385-400.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Swayze et al., "The Medicinal Chemistry of Oligonucleotides" Antisense Drug Technology: Principles, Strategies, and Applications, 2nd ED. (2007) 143-182.
Tanskanen et al., "Senile systemic amyloidosis affects 25% of the very aged and associates with genetic variation in alpha2-macroglobulin and tau: A population-based autopsy study" Ann Med. (2008) 40(3): 232-239.
Taylor et al., "Curbing activation: proprotein convertases in homeostasis and pathology" FASEB J. (2003) 17: 1215-1227.
Timms et al., "A mutation in PCSK9 causing autosomal-dominant hypercholesterolemia in a Utah pedigree." Hum. Genet. (2004) 114(4): 349-353.
Tober et al., "Self-Metathesis of Polyol Allyl Ethers towards Carbohydrate-Based Oligohydroxy Derivatives" Eur. J. Org. Chem. (2013) 3: 566-577.
Tomiya et al., "Liver-targeting of primaquine-(poly-c-glutamic acid) and its degradation in rat hepatocytes" Bioorganic & Medicinal Chemistry (2013) 21: 5275-5281.
Toyokuni et al., "Synthetic vaccines: I. Synthesis of multivalent Tn antigen cluster-lysyllysine conjugates" Tetrahedron Lett (1990) 31(19): 2673-2676.
Trappeniers et al., "6'-derivatised alpha-GalCer analogues capable of inducing strong CD1d-mediated Th1-biased NKT cell responses in mice" J Am Chem Soc. (2008) 130(49):16468-9.
Valentijn et al., "Solid-phase Synthesis of Lysine-based Cluster Galactosides with High Affinity for the Asialoglycoprotein Receptor" Tetrahedron (1997) 53(2): 759-770.
Van Rossenberg et al., "Stable polyplexes based on arginine-containing oligopeptides for in vivo gene delivery" Gene Ther (2004) 11: 457-464.
Wahlestedt et al., "Potent and nontoxic antisense oligonucleotide containing locked nucleic acids" Proc. Natl. Acad. Sci. USA (2000) 97: 5633-5638.
Wang et al., "Expression of the Eukaryotic Translation Initiation Factors 4E and 2a in Non-Hodgkin's Lymphomas" Am. J. Pathol. (1999) 155(1): 247-255.
Weber et al., "Design and synthesis of P2-P1'-linked macrocyclic human renin inhibitors" J. Med. Chem. (1991) 34(9): 2692-2701.
Weinberger et al., "Identification of Human Glucocorticoid Receptor Complementary DNA Clones by Epitope Selection" Science (1985) 228: 740-742.
Westerlind et al., "Ligands of the asialoglycoprotein receptor for targeted gene delivery, part 1: Synthesis of and binding studies with biotinylated cluster glycosides containing N-acetylgalactosamine" Glycoconjugate Journal (2004) 21: 227-241.
Winkler et al., "Oligonucleotide conjugates for therapeutic applications" Ther Deliv. (2013) 4(7):791-809.
Woolf et al., "Specificity of antisense oligonucleotides in vivo" PNAS (1992) 89: 7305-7309.
Wu et al., "A New N-Acetylgalactosamine Containing Peptide as a Targeting Vehicle for Mammalian Hepatocytes Via Asialoglycoprotein Receptor Endocytosis" Current Drug Delivery (2004) 1: 119-127.
Yadav et al., "Carbohydrate functionalized iron(III) complexes as biomimetic siderophores." Chem Commun (Camb) (2012) 48(11): 1704-1706.
Yang et al., "STAT3 complements defects in an interferon-resistant cell line: Evidence for an essential role for STAT3 in interferon signaling and biological activities" PNAS (1998) 95: 5568-5572.
Zhao et al., "Synthesis and preliminary biochemical studies with 5'-deoxy-5'-methylidyne phosphonate linked thymidine oligonucleotides" Tetrahedron Letters (1996) 37(35): 6239-6242.
Zhong et al., "Stat3 and Stat4: Memers of the family of signal transducers and activators of transcription" PNAS (1994) 91: 4806-4810.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
Zhou et al., "Proteolytic processing in the secretory pathway." J. Biol. Chem. (1999) 274(30): 20745-20748.
European Search Report for Application 14792010.2 dated Jan. 18, 2017.
Extended European Search Report for 15785492.8 dated Nov. 8, 2017.
Extended European Search Report for 19160031.1 dated Aug. 22, 2019.
Extended European Search Report for 19197023.5 dated Mar. 20, 2020.
International Search Report for Application PCT/US12/52884 dated Nov. 20, 2012.
International Search Report for Application PCT/US14/36460 dated Oct. 10, 2014.
International Search Report for Application PCT/US14/36466 dated Dec. 1, 2014.
International Search Report for Application PCT/US14/36462 dated Dec. 23, 2014.
International Search Report for Application PCT/US14/56630 dated Dec. 24, 2014.
International Search Report for Application PCT/US14/43731 dated Dec. 10, 2014.
International Search Report for Application PCT/US14/36463 dated Dec. 30, 2014.
International Search Report for ApplicationPCT/US17/55481 dated Dec. 28, 2017.
Prakash et al., "Solid-phase synthesis of 5'-triantennary N-acetylgalactosamine conjugated antisense oligonucleotides using phosphoramidite chemistry" Bioorg Med Chem Lett (2015) 25: 4127-4130.

\* cited by examiner

SEQUENCE LISTING

<160> NUMBER OF SEQ ID NOS: 1

<210> SEQ ID NO 1
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 1
tgctccgttg gtgcttgttc       20

METHOD OF CONJUGATING OLIGOMERIC COMPOUNDS

SEQUENCE LISTING

The present application is being filed along with a Sequence Listing in electronic format. The Sequence Listing is provided as a file entitled DVCM0044USASEQ_ST25.txt, created on Mar. 12, 2019 which is 4 Kb in size. The information in the electronic format of the sequence listing is incorporated herein by reference in its entirety.

FIELD OF THE INVENTION

The present disclosure relates to methods of conjugating oligomeric compounds and intermediates used in such methods. In particular, the present methods provide solid phase methods of coupling a phosphoramidite functionalized conjugate group to an oligomeric compound. The present methods provide enhancements compared to previously reported methods.

BACKGROUND OF THE INVENTION

The synthesis of conjugated oligomeric compounds has been reported in numerous publications (see for example Maier et al., "Synthesis of Antisense Oligonucleotides Conjugated to a Multivalent Carbohydrate Cluster for Cellular Targeting," *Bioconjugate Chemistry*, 2003, (14): 18-29; Rensen et al., "Design and Synthesis of Novel N-Acetylgalactosamine-Terminated Glycolipids for Targeting of Lipoproteins to the Hepatic Asiaglycoprotein Receptor," *J. Med. Chem.* 2004, (47): 5798-5808; U.S. Pat. Nos. 8,507,661; and 9,127,276).

SUMMARY OF THE INVENTION

The present invention provides methods of conjugating an oligomeric compound to provide a conjugated oligomeric compound comprising:

providing a solid support bound oligomeric compound having a primary hydroxyl group;

contacting the solid support bound oligomeric compound with a solution comprising a phosphoramidite functionalized conjugate group having the formula:

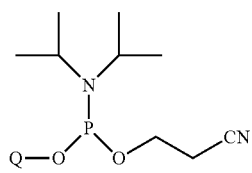

wherein Q is a conjugate group;

recirculating the solution to provide a phosphite linkage between the conjugate group and the oligomeric compound;

oxidizing the phosphite linkage to a phosphate or thiophosphate linkage;

treating the solid support with ammonia to provide the conjugated oligomeric compound having the formula:

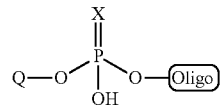

wherein X is O or S;

wherein:

the solution for the contacting step comprises from 1.5 to 2.0 equivalents of the phosphoramidite functionalized conjugate group, the steps of contacting, recirculating and oxidizing are repeated for one, two or three additional cycles and the recirculating step is performed from about 5 to about 10 minutes; or the solution for the contacting step comprises from 1.5 to 2.0 equivalents of the phosphoramidite functionalized conjugate group and the recirculating step is performed from about 5 to about 180 minutes; or the solution for the contacting step comprises from 2.5 to 3.5 equivalents of the phosphoramidite functionalized conjugate group and the recirculating time is from 20 to 180 minutes.

In certain embodiments, the conjugation of the oligomeric compound provides at least an 85% yield based on the actual number of equivalents of solid support bound oligomeric compound having a primary hydroxyl group. In certain embodiments, the conjugation of the oligomeric compound provides at least a 90% yield based on the actual number of equivalents of solid support bound oligomeric compound having a primary hydroxyl group. In certain embodiments, the conjugation of the oligomeric compound provides at least a 94% yield based on the actual number of equivalents of solid support bound oligomeric compound having a primary hydroxyl group.

In certain embodiments, the solution for the contacting step comprises about 1.75 equivalents of the phosphoramidite functionalized conjugate group and the steps of contacting, recirculating and oxidizing are repeated for one, two or three additional cycles. In certain embodiments, the solution for the contacting step comprises about 1.75 equivalents of the phosphoramidite functionalized conjugate group, the steps of contacting, recirculating and oxidizing are repeated for one, two or three additional cycles and the recirculating step is performed for about 5 minutes for each cycle. In certain embodiments, the solution for the contacting step comprises 1.75 equivalents of the phosphoramidite functionalized conjugate group, the steps of contacting, recirculating and oxidizing are repeated for two additional cycles and the recirculating step is performed for 5 minutes for each cycle.

In certain embodiments, the solution comprises from about 2.5 to about 3.5 equivalents of the phosphoramidite functionalized conjugate group and the recirculating step is performed for about 20 to 40 minutes. In certain embodiments, the solution comprises from about 2.5 to about 3.5 equivalents of the phosphoramidite functionalized conjugate group and the recirculating step is performed for about 30 minutes. In certain embodiments, the solution comprises from 2.8 to 3.0 equivalents of the phosphoramidite functionalized conjugate group and the recirculating step is performed for about 30 minutes.

In certain embodiments, the solution for the contacting step comprises about 1.75 equivalents of the phosphoramidite functionalized conjugate group and the step of recirculating is performed for from about 140 to 200 minutes. In certain embodiments, the solution for the contacting step comprises about 1.75 equivalents of the phosphoramidite functionalized conjugate group and the step of recirculating is performed for about 180 minutes.

In certain embodiments, the phosphoramidite functionalized conjugate group has the formula:

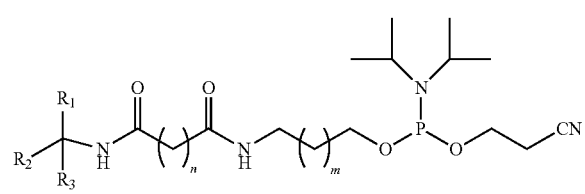

wherein:
  n is from 4 to 10;
  m is from 1 to 8;

$R_1$, $R_2$ and $R_3$ are each a linked GalNAc group having the formula:

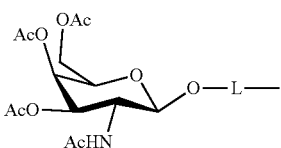

wherein each L is a linking group comprising an alkyl chain interrupted by one or more groups independently selected from —O—, —N(H)—, —C(=O)— and —O—P(=O)(—OH)—O—. In certain embodiments, the phosphoramidite functionalized conjugate group has the formula:

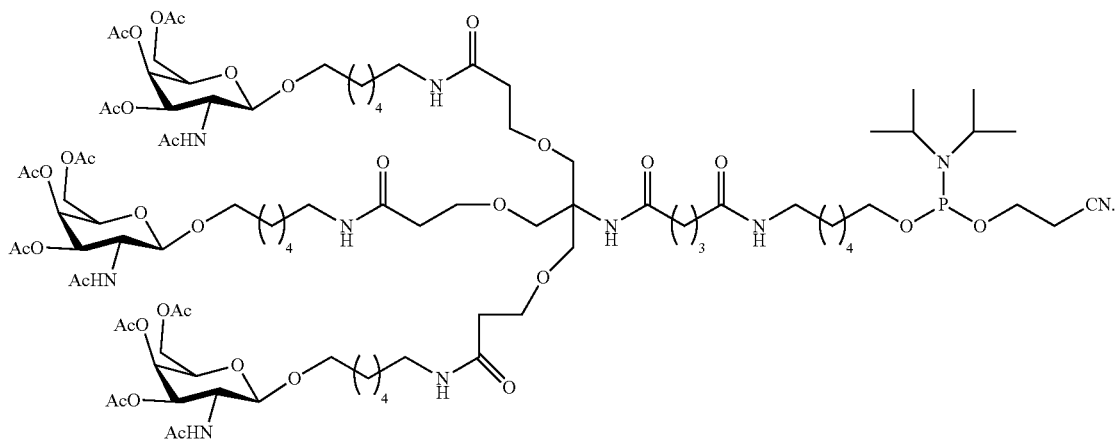

In certain embodiments, the conjugated oligomeric compound has the formula:

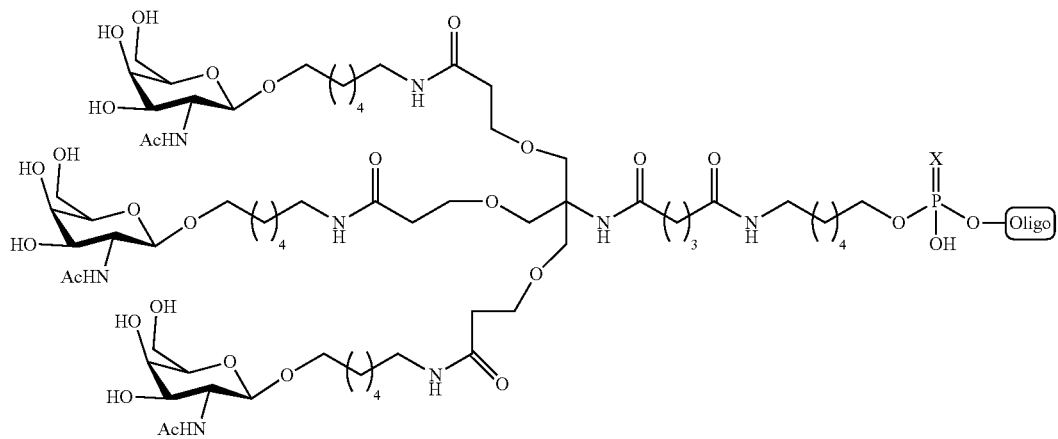

wherein X is O or S.

In certain embodiments, the solid support bound oligomeric compound having a primary hydroxyl group is prepared using standard solid phase protocols on an automated synthesizer.

In certain embodiments, the contacting step is performed in the presence of 4,5-dicyanoimidazole and N-methylimidazole in acetonitrile.

In certain embodiments, X is S. In certain embodiments, the oxidizing step is performed using phenylacetyl disulfide. In certain embodiments, the oxidizing step is performed using a solution of 0.2 molar phenylacetyl disulfide in acetonitrile:3'-picoline (1:1; v/v). In certain embodiments, the oxidizing step is performed using xanthane hydride.

In certain embodiments, X is O. In certain embodiments, n the oxidizing step is performed using iodine.

In certain embodiments, the treatment with ammonia is performed using from about 28% to about 30% aqueous ammonium hydroxide.

In certain embodiments, the conjugated oligomeric compound comprises a sequence of from 8 to 30 linked monomer subunits. In certain embodiments, the conjugated oligomeric compound comprises a sequence of from 16 to 20 linked monomer subunits. In certain embodiments, the conjugated oligomeric compound comprises a sequence of from 16 to 22 linked monomer subunits.

In certain embodiments, the primary hydroxyl group is a 5'-terminal hydroxyl group. In certain embodiments, the primary hydroxyl group is a 5'-terminal hydroxyl group on an optionally protected β-D-ribonucleoside, β-D-2'-deoxyribonucleoside or a modified nucleoside. In certain embodiments, the primary hydroxyl group is a primary hydroxyl group on a sugar surrogate.

In certain embodiments, the method is performed on a 200 to 800 mmol scale based on the loading of the solid support. In certain embodiments, the method is performed on at least a 200 mmol scale based on the loading of the solid support.

The present invention further provides methods for the preparation of conjugated oligomeric compounds to provide conjugated oligomeric compounds comprising:

providing a solid support bound oligomeric compound having a primary hydroxyl group;

contacting the solid support bound oligomeric compound with a solution comprising a phosphoramidite functionalized conjugate group having the formula:

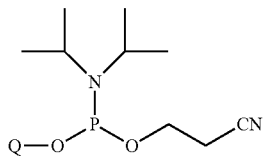

wherein Q is a conjugate group;

recirculating the solution to provide a phosphite linkage between the conjugate group and the oligomeric compound;

oxidizing the phosphite linkage to a phosphate or thiophosphate linkage;

treating the solid support with ammonia to provide the conjugated oligomeric compound having the formula:

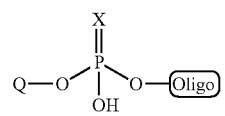

wherein X is O or S;

wherein:

the solution for the contacting step comprises from 1.5 to 2.0 equivalents of the phosphoramidite functionalized conjugate group, the steps of contacting, recirculating and oxidizing are repeated for one, two or three additional cycles and the recirculating step is performed from about 5 to about 10 minutes; or the solution for the contacting step comprises from 2.5 to 3.5 equivalents of the phosphoramidite functionalized conjugate group and the recirculating time is from 20 to 40 minutes.

In certain embodiments, the conjugation of the oligomeric compound provides at least an 85% yield based on the actual number of equivalents of solid support bound oligomeric compound having a primary hydroxyl group. The 85% calculation is based on the coupling efficiency of the conjugation step and not inclusive of the yield calculations for the synthesis of the oligomeric compound on the solid support. In certain embodiments, the conjugation of the oligomeric compound provides at least an 90% yield based on the actual number of equivalents of solid support bound oligomeric compound having a primary hydroxyl group. The 90% calculation is based on the coupling efficiency of the conjugation step and not inclusive of the yield calculations for the synthesis of the oligomeric compound on the solid support.

In certain embodiments, the yield of conjugated oligomeric compound is at least 85%. In certain embodiments, the yield of conjugated oligomeric compound is at least 90%. In certain embodiments, the yield of conjugated oligomeric compound is at least 95%.

In certain embodiments, the solution for the contacting step comprises about 1.75 equivalents of the phosphoramidite functionalized conjugate group and the steps of contacting, recirculating and oxidizing are repeated for one, two or three additional cycles. In certain embodiments, the solution for the contacting step comprises about 1.75 equivalents of the phosphoramidite functionalized conjugate group, the steps of contacting, recirculating and oxidizing are repeated for one, two or three additional cycles and the recirculating step is performed for about 5 minutes for each cycle. In certain embodiments, the solution for the contacting step comprises 1.75 equivalents of the phosphoramidite functionalized conjugate group, the steps of contacting, recirculating and oxidizing are repeated for two additional cycles and the recirculating step is performed for 5 minutes for each cycle.

In certain embodiments, the contacting step is performed only once, the solution comprises from about 2.5 to about 3.5 equivalents of the phosphoramidite functionalized conjugate group and the recirculating step is performed for about 20 to 40 minutes. In certain embodiments, the contacting step is performed only once, the solution comprises from about 2.5 to about 3.5 equivalents of the phosphoramidite functionalized conjugate group and the recirculating step is performed for about 30 minutes. In certain embodiments, the contacting step is performed only once, the solution comprises from 2.8 to 3.0 equivalents of the phosphoramidite functionalized conjugate group and the recirculating step is performed for 30 minutes.

In certain embodiments, the phosphoramidite functionalized conjugate group has the formula:

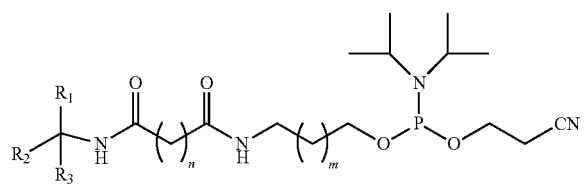

wherein:

n is from 4 to 10;

m is from 1 to 8

$R_1$, $R_2$ and $R_3$ are each a linked GalNAc group having the formula:

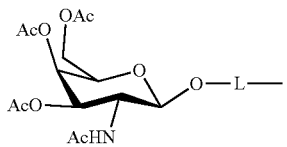

wherein:

each L is a linking group comprising an alkyl chain interrupted by one or more groups independently selected from —O—, —N(H)—, —C(=O)— and —O—P(=O)(—OH)—O—.

In certain embodiments, each L is a linking group comprising an alkyl chain interrupted by one or more groups independently selected from —O—, —N(H)— and —C(=O)—.

In certain embodiments, the phosphoramidite functionalized conjugate group has the formula:

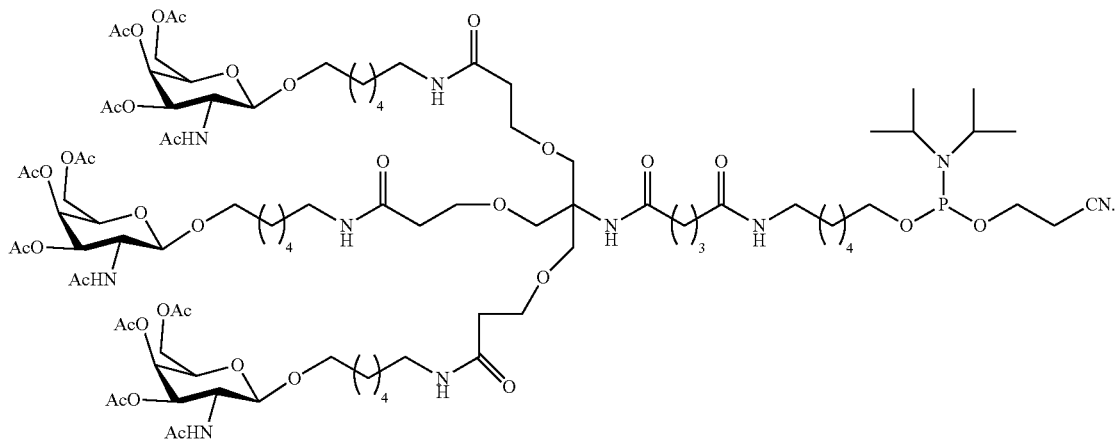

In certain embodiments, the conjugated oligomeric compound has the formula:

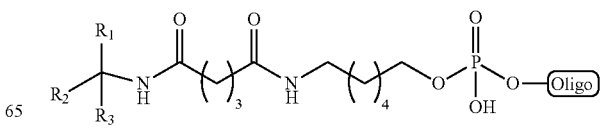

wherein:

R$_1$, R$_2$ and R$_3$ are each a linked GalNAc group; and

X is O or S.

In certain embodiments, the conjugated oligomeric compound has the formula:

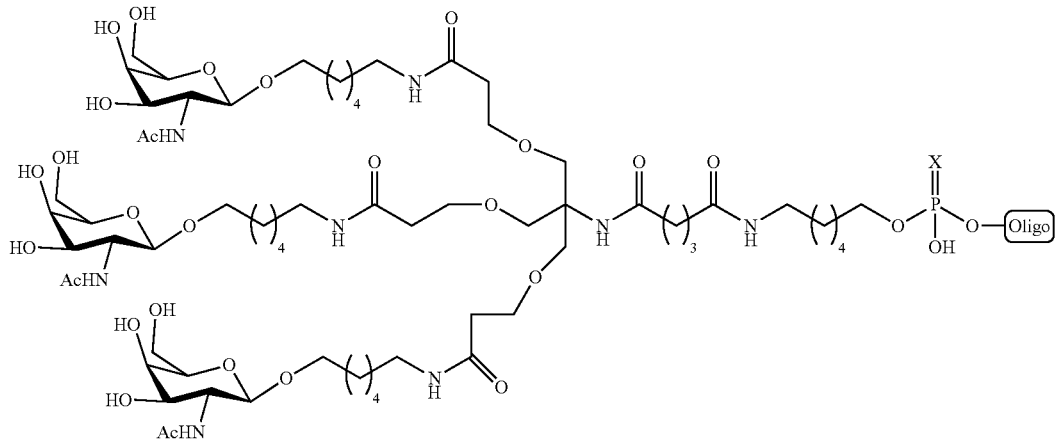

wherein X is O or S.

In certain embodiments, the solid support bound oligomeric compound having a primary hydroxyl group is prepared using standard solid phase protocols on an automated synthesizer.

In certain embodiments, the contacting step performed in the presence of 4,5-dicyanoimidazole and N-methylimidazole in acetonitrile.

In certain embodiments, X is S. In certain embodiments, the oxidizing step is performed using phenylacetyl disulfide. In certain embodiments, the oxidizing step is performed using a solution of 0.2 molar phenylacetyl disulfide in acetonitrile:3'-picoline (1:1; v/v). In certain embodiments, the oxidizing step is performed using xanthane hydride.

In certain embodiments, X is O. In certain embodiments, the oxidizing step is performed using iodine.

In certain embodiments, the treatment with ammonia is performed using from about 28% to about 30% aqueous ammonium hydroxide.

In certain embodiments, the conjugated oligomeric compound comprises a sequence of from 8 to 30 linked monomer subunits.

In certain embodiments, the primary hydroxyl group is a 5'-terminal hydroxyl group. In certain embodiments, the primary hydroxyl group is a 5'-terminal hydroxyl group on an optionally protected β-D-ribonucleoside, β-D-2'-deoxyribonucleoside or a modified nucleoside. In certain embodiments, the primary hydroxyl group is a primary hydroxyl group on a sugar surrogate.

In certain embodiments, The present methods are performed on a 200 to 600 mmol scale based on the loading of the solid support. In certain embodiments, The present methods are performed on a 200 to 800 mmol scale based on the loading of the solid support. In certain embodiments, The present methods are performed on at least a 200 mmol scale based on the loading of the solid support. In certain embodiments, The present methods are performed on at least a 400 mmol scale based on the loading of the solid support. In certain embodiments, The present methods are performed on at least a 600 mmol scale based on the loading of the solid support.

In certain embodiments, a compound is provided having the formula:

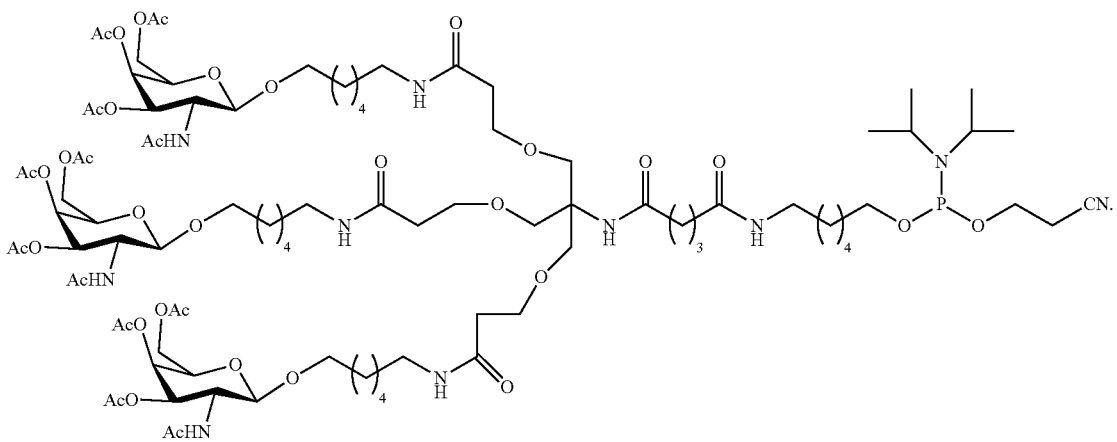

DETAILED DESCRIPTION OF THE INVENTION

Provided herein are methods for preparing conjugated oligomeric compounds and intermediates used in such methods. The methods include solid support conjugation of an oligomeric compound having a free hydroxyl group to a phosphoramidite functionalized conjugate group. The solid phase conjugation on an automated synthesizer which eliminates post cleavage issues such as further solution phase reactions and multiple purification steps when doing conjugation in solution phase (see Ex. 9). The present methods also provide improved yields for the conjugated oligomeric compounds compared to using standard solid phase protocols.

Standard solid phase protocols include reacting free hydroxyl groups on a solid support, such as provided by a Unylinker functionalized solid support or one or more linked monomeric subunits linked to a solid support, with a phosphoramidite linked monomer subunit to begin or add to a growing sequence. The present methods utilize this solid phase approach to add a phosphoramidite functionalized conjugate group rather than a monomer subunit such as a nucleoside. Typically, the free hydroxyl group is a 5'-terminal hydroxyl group. After contacting the free hydroxyl group with a solution comprising the selected phosphoramidite the solution is recirculated for a time. The solid support is treated with an oxidizing solution to convert the phosphite linkage to either a phosphodiester linkage or a phosphorothioate linkage depending on the choice of oxidizing solution used. Then the crude oligomeric compound is deblocked and cleaved using ammonia. The solid support is rinsed between these steps. However, when these protocols were initially investigated for coupling of phosphoramidite functionalized conjugate groups such as THA, the yields were too low for the method to be viable. Previous work also reported poor yields for coupling of Gal$_3$Chol amidite to the 5'-end of a resin-bound oligonucleotide (see Maier et al., "Synthesis of Antisense Oligonucleotides Conjugated to a Multivalent Carbohydrate Cluster for Cellular Targeting," *Bioconjugate Chemistry*, 2003, (14): 18-29).

The present methods use the standard protocols for synthesizing a desired oligomeric compound (protocol may differ for various monomer subunits, see U.S. Patent Publication No.: US 2015/0218205) on a solid support. The standard protocol has been modified for the last coupling of a phosphoramidite functionalized conjugate group. The solid support is contacted with a solution comprising a phosphoramidite functionalized conjugate group and the solution is recirculated through the solid support for a time. The resulting phosphite linkage is then oxidized to a phosphodiester or phosphorothioate linkage. In certain embodiments, the steps of contacting, recycling and oxidizing are repeated resulting in an increase in the yield. In certain embodiments, a solution having about 1.75 equivalents of the phosphoramidite functionalized conjugate group is used for coupling (contacting step) of the conjugate group to the solid support bound oligomeric compound. After contacting the solid support the solution is recirculated for about 5 minutes and then the solid support is rinsed, contacted with an oxidizing solution, rinsed again. In certain embodiments, contacting, recirculating and oxidizing steps are repeated twice for a total of three cycles. The solid support bound conjugated oligomeric compound is deprotected and treated with ammonia to provide the free conjugated oligomeric compound. Performing the steps of coupling, recirculating and oxidizing with 1.75 equivalents of phosphoramidite functionalized conjugate group unexpectedly provided an increased yield compared to the standard single cycle protocol. Preparing a 20mer oligomeric compound on solid support following standard protocols of 1.75 equivalents (amidite functionalized conjugate) and recirculating for 15 minutes on a 1.1 mmol scale synthesis provided an overall yield of 50% with the coupling efficiency at about 80%.

In certain embodiments, the solid support bound oligomeric compound is reacted with about 1.75 equivalents of the phosphoramidite functionalized conjugate group, as a solution (0.2M) in a suitable solvent such as acetonitrile. The coupling solution is recirculated for a time such as about 5 minutes to about 10 minutes and the solid support is rinsed and treated with an oxidizing agent. In certain embodiments, the steps of reacting with a phosphoramidite functionalized conjugate group, recirculating, rinsing and oxidation are repeated twice before deblocking and treating the solid support with ammonium hydroxide to cleave the conjugated oligomeric compound.

In certain embodiments, performing the contacting, recirculating and oxidizing steps only once while increasing the equivalents of phosphoramidite functionalized conjugate group and also increasing the recirculation time produced increased yields over standard protocols. In certain embodiments, a solution having about 2.9 equivalents of the phosphoramidite functionalized conjugate group is used for coupling (contacting step) of the phosphoramidite functionalized conjugate group to the solid support bound oligomeric compound. After contacting the solid support the solution is recirculated for about 30 minutes and then the solid support is rinsed and contacted with an oxidizing solution followed by deprotection and cleavage to provide the crude conjugated oligomeric compound. Performing the conjugation with increased equivalents of phosphoramidite functionalized conjugate group and increased recycle time provided an increased yield compared to standard protocols.

In certain embodiments, phosphoramidite functionalized conjugate groups amenable to the present invention have the formula:

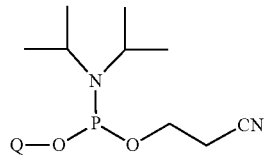

wherein Q is a conjugate group.

In certain embodiments, phosphoramidite functionalized conjugate groups amenable to the present invention have the formula:

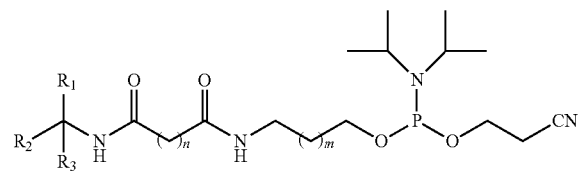

wherein $R_1$, $R_2$ and $R_3$ are each a linked GalNAc group.

In certain embodiments, the phosphoramidite functionalized conjugate group has the formula:

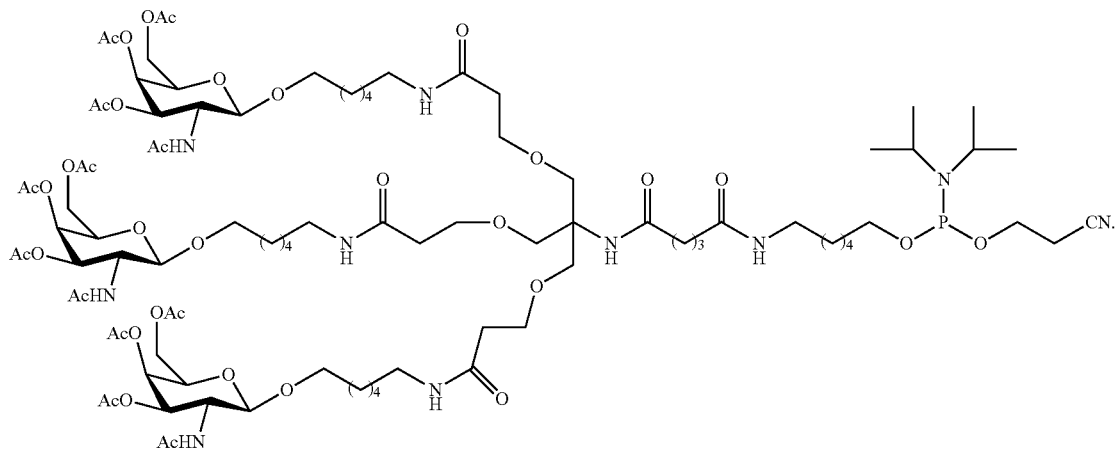

In certain embodiments, conjugated oligomeric compounds are prepared having the formula:

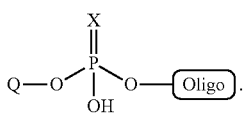

wherein X is O or S.

In certain embodiments, conjugated oligomeric compounds are prepared having the formula:

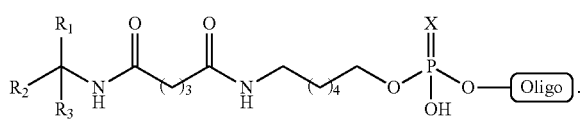

wherein X is O or S.

In certain embodiments, conjugated oligomeric compounds are prepared having the formula:

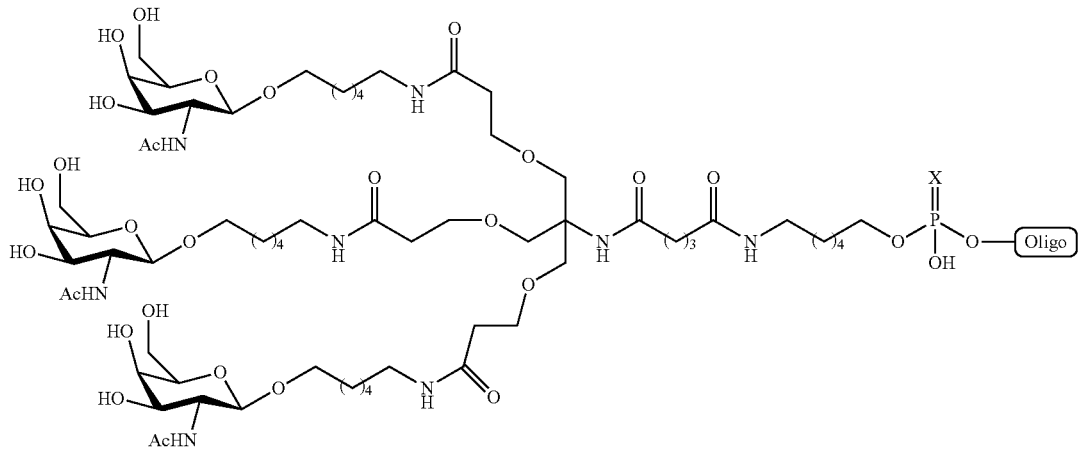

wherein X is O or S.

In certain embodiments, the present solid phase conjugation methods provide advantages over previous solid phase and solution phase methods for coupling conjugate groups to an oligomeric compound. A major advantage over solution phase conjugations is that fewer reaction and purification steps are required. Once an oligomeric compound is cleaved from the solid support it is purified whether conjugated or not. Solution phase methods require further conjugation and then a second purification step. The present methods also provide an improved impurity profile compared to solution phase methods by eliminating some of the impurities encountered with solution phase conjugation methods currently being used. The present methods provide an increased yield compared to standard phosphoramidite coupling protocols.

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

As used herein, "conjugate" or "conjugate group" means an atom or group of atoms capable of being bound to a parent compound such as an oligonucleotide or an oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties. In certain embodiments, a conjugate group comprises a reactive conjugate cluster.

As used herein, "carbohydrate cluster" means a compound having two or more carbohydrate residues attached to a scaffold or linker group (referred to herein as a branching group). (see, e.g., Maier et al., "Synthesis of Antisense Oligonucleotides Conjugated to a Multivalent Carbohydrate Cluster for Cellular Targeting," Bioconjugate Chemistry, 2003, (14): 18-29, which is incorporated herein by reference in its entirety, or Rensen et al., "Design and Synthesis of Novel N-Acetyl-galactosamine-Terminated Glycolipids for Targeting of Lipoproteins to the Hepatic Asialglycoprotein Receptor," J. Med. Chem. 2004, (47): 5798-5808, for examples of carbohydrate conjugate clusters).

As used herein, "carbohydrate" means a naturally occurring carbohydrate, a modified carbohydrate, or a carbohydrate derivative. In general, a naturally occurring carbohydrate is any of various compounds containing carbon, hydrogen, and oxygen (such as sugars, starches, and celluloses) most of which are formed by green plants and which constitute a major class of animal foods. In general, a naturally occurring carbohydrate is any of various compounds containing carbon, hydrogen, and oxygen (such as sugars, starches, and celluloses) most of which are formed by green plants and which constitute a major class of animal foods.

As used herein, "modified carbohydrate" means any carbohydrate having one or more chemical modifications relative to naturally occurring carbohydrates. In certain embodiments, a carbohydrate cluster comprises a reactive conjugate cluster.

As used herein, "carbohydrate derivative" means any compound which may be synthesized using a carbohydrate as a starting material or intermediate.

In certain embodiments, a carbohydrate cluster can be covalently attached to a parent compound to enhance one or more properties of the parent compound. As used herein, "parent compound" means a small molecule, a large molecule or a polymer capable of having a carbohydrate cluster attached thereto. In certain embodiments, the parent compound is a drug such as a naturally occurring or synthetic small molecule, a naturally occurring or synthetic large molecule, or a naturally occurring or synthetic polymer. In certain embodiments, a parent compound is a naturally occurring or synthetic peptide or a naturally occurring or synthetic nucleic acid molecule. In certain embodiments, a parent compound is an oligomeric compound or an oligonucleotide.

As used herein, "conjugate linker" or "linker" in the context of a conjugate group means a portion of a conjugate group comprising any atom or group of atoms and which covalently link the conjugate group to a parent compound such as an oligomeric compound or an antisense oligonucleotide. In certain embodiments, a conjugate group is attached directly to a parent compound without a linker group (the branching group is attached to the parent compound directly).

Conjugate groups have at least one reactive group for forming covalent attachment to a parent compound such as an oligomeric compound or an antisense oligonucleotide. In certain embodiments, the point of attachment on the oligomeric compound is the 3'-oxygen atom of the 3'-hydroxyl group of the 3' terminal nucleoside of the oligomeric compound. In certain embodiments the point of attachment on the oligomeric compound is the 5'-oxygen atom of the 5'-hydroxyl group of the 5' terminal nucleoside of the oligomeric compound. In certain embodiments the point of attachment on the oligomeric compound is a terminal free hydroxyl group on the oligomeric compound. In certain embodiments, the bond for forming attachment to the oligomeric compound is a cleavable bond. In certain such embodiments, such cleavable bond constitutes all or part of a cleavable moiety.

Representative publications that teach the preparation of certain of the above noted conjugates, conjugated antisense compounds, tethers, linkers, branching groups, ligands, cleavable moieties as well as other modifications include without limitation, BIESSEN et al., "The Cholesterol Derivative of a Triantennary Galactoside with High Affinity for the Hepatic Asialoglycoprotein Receptor: a Potent Cholesterol Lowering Agent" J. Med. Chem. (1995) 38:1846-1852, BIESSEN et al., "Synthesis of Cluster Galactosides with High Affinity for the Hepatic Asialoglycoprotein Receptor" J. Med. Chem. (1995) 38:1538-1546, LEE et al., "New and more efficient multivalent glyco-ligands for asialoglycoprotein receptor of mammalian hepatocytes" Bioorganic & Medicinal Chemistry (2011) 19:2494-2500, RENSEN et al., "Determination of the Upper Size Limit for Uptake and Processing of Ligands by the Asialoglycoprotein Receptor on Hepatocytes in Vitro and in Vivo" J. Biol. Chem. (2001) 276(40):37577-37584, RENSEN et al., "Design and Synthesis of Novel N-Acetylgalactosamine-Terminated Glycolipids for Targeting of Lipoproteins to the Hepatic Asialoglycoprotein Receptor" J. Med. Chem. (2004) 47:5798-5808, SLIEDREGT et al., "Design and Synthesis of Novel Amphiphilic Dendritic Galactosides for Selective Targeting of Liposomes to the Hepatic Asialoglycoprotein Receptor" J. Med. Chem. (1999) 42:609-618, and Valentijn et al., "Solid-phase synthesis of lysine-based cluster galactosides with high affinity for the Asialoglycoprotein Receptor" Tetrahedron, 1997, 53(2), 759-770, each of which is incorporated by reference herein in its entirety.

In certain embodiments, oligomeric compounds prepared as per the methods of the present invention are antisense compounds. In such embodiments, the oligomeric compound is complementary to a target nucleic acid. In certain embodiments, a target nucleic acid is an RNA. In certain embodiments, a target nucleic acid is a non-coding RNA. In certain embodiments, a target nucleic acid encodes a protein. In certain embodiments, a target nucleic acid is selected from a mRNA, a pre-mRNA, a microRNA, a non-coding RNA, including small non-coding RNA, and a promoter-directed RNA. In certain embodiments, oligomeric compounds are at least partially complementary to more than one target nucleic acid. For example, oligomeric compounds of the present invention may be microRNA mimics, which typically bind to multiple targets.

In certain embodiments, oligomeric compounds prepared as per the methods of the present invention are RNAi compounds. In certain embodiments, oligomeric oligonucleotides comprising conjugates described herein are ssRNA compounds. In certain embodiments, oligomeric compounds prepared as per the methods of the present invention are paired with a second oligomeric compound to form an siRNA. In certain such embodiments, the second oligomeric compound also comprises a conjugate. In certain embodiments, the second oligomeric compound is any modified or unmodified nucleic acid. In certain embodiments, the oligomeric compounds prepared as per the methods of the present invention are the antisense strand in an siRNA compound. In certain embodiments, the oligomeric compounds prepared as per the methods of the present invention are the sense strand in an siRNA compound.

As used herein the term "alkyl," refers to a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred. The term "lower alkyl" as used herein includes from 1 to about 6 carbon atoms. Alkyl groups as used herein may optionally include one or more further substituent groups.

As used herein the term "alkenyl," refers to a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein the term "alkynyl," refers to a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein the term "aliphatic," refers to a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein the term "alicyclic" refers to a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein the terms "aryl" and "aromatic," refer to a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein the terms "heteroaryl," and "heteroaromatic," refer to a radical comprising a mono- or poly-cyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein the term "acyl," refers to a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein the term "hydrocarbyl" includes radical groups that comprise C, O and H. Included are straight, branched and cyclic groups having any degree of saturation. Such hydrocarbyl groups can include one or more additional heteroatoms selected from N and S and can be further mono or poly substituted with one or more substituent groups.

As used herein the term "protecting group," refers to a labile chemical moiety which is known in the art to protect reactive groups including without limitation, hydroxyl, amino and thiol groups, against undesired reactions during synthetic procedures. Protecting groups are typically used selectively and/or orthogonally to protect sites during reactions at other reactive sites and can then be removed to leave the unprotected group as is or available for further reactions. Protecting groups as known in the art are described generally in Greene's Protective Groups in Organic Synthesis, 4th edition, John Wiley & Sons, New York, 2007.

Groups can be selectively incorporated into oligomeric compounds as provided herein as precursors. For example an amino group can be placed into a compound as provided herein as an azido group that can be chemically converted to the amino group at a desired point in the synthesis. Generally, groups are protected or present as precursors that will be inert to reactions that modify other areas of the parent molecule for conversion into their final groups at an appropriate time. Further representative protecting or precursor groups are discussed in Agrawal et al., *Protocols for Oligonucleotide Conjugates*, Humana Press; New Jersey, 1994, 26, 1-72.

The term "orthogonally protected" refers to functional groups which are protected with different classes of protecting groups, wherein each class of protecting group can be removed in any order and in the presence of all other classes (see, Barany et al., *J. Am. Chem. Soc.*, 1977, 99, 7363-7365; Barany et al., *J. Am. Chem. Soc.*, 1980, 102, 3084-3095). Orthogonal protection is widely used in for example automated oligonucleotide synthesis. A functional group is deblocked in the presence of one or more other protected functional groups which is not affected by the deblocking procedure. This deblocked functional group is reacted in some manner and at some point a further orthogonal protecting group is removed under a different set of reaction conditions. This allows for selective chemistry to arrive at a desired compound or oligomeric compound.

Examples of hydroxyl protecting groups include without limitation, acetyl, t-butyl, t-butoxymethyl, methoxymethyl, tetrahydropyranyl, 1-ethoxyethyl, 1-(2-chloroethoxy)ethyl, p-chlorophenyl, 2,4-dinitrophenyl, benzyl, 2,6-dichlorobenzyl, diphenylmethyl, p-nitrobenzyl, bis(2-acetoxyethoxy) methyl (ACE), 2-trimethylsilylethyl, trimethylsilyl, triethylsilyl, t-butyldimethylsilyl, t-butyldiphenylsilyl, triphenylsilyl, [(triisopropylsilyl)oxy]methyl (TOM), benzoylformate, chloroacetyl, trichloroacetyl, trifluoroacetyl, pivaloyl, benzoyl, p-phenylbenzoyl, 9-fluorenylmethyl carbonate, mesylate, tosylate, triphenylmethyl (trityl), monomethoxytrityl, dimethoxytrityl (DMT), trimethoxytrityl, 1(2-fluorophenyl)-4-methoxypiperidin-4-yl (FPMP), 9-phenylxanthine-9-yl (Pixyl) and 9-(p-methoxyphenyl) xanthine-9-yl (MOX). Wherein more commonly used hydroxyl protecting groups include without limitation, benzyl, 2,6-dichlorobenzyl, t-butyldimethylsilyl, t-butyldiphenylsilyl, benzoyl, mesylate, tosylate, dimethoxytrityl (DMT), 9-phenylxanthine-9-yl (Pixyl) and 9-(p-methoxyphenyl)xanthine-9-yl (MOX).

Examples of amino protecting groups include without limitation, carbamate-protecting groups, such as 2-trimethylsilylethoxycarbonyl (Teoc), 1-methyl-1-(4-biphenylyl) ethoxycarbonyl (Bpoc), t-butoxycarbonyl (BOC), allyloxycarbonyl (Alloc), 9-fluorenylmethyloxycarbonyl (Fmoc), and benzyloxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

Examples of thiol protecting groups include without limitation, triphenylmethyl (trityl), benzyl (Bn), and the like.

The terms "substituent" and "substituent group," as used herein, are meant to include groups that are typically added to a parent compounds or to further substituted substituent groups to enhance one or more desired properties or provide other desired effects. Substituent groups can be protected or unprotected and can be added to one available site or many available sites on a parent compound. As an example if a benzene is substituted with a substituted alky it will not have any overlap with a benzene that is substituted with substituted hydroxyl. In such an example the alkyl portion of the substituted alkyl is covalently linked by one of its carbon atoms to one of the benzene carbon atoms. If the alky is $C_1$ and it is substituted with a hydroxyl substituent group (substituted alkyl) then the resultant compound is benzyl alcohol ($C_6H_5CH_2OH$). If the benzene were substituted with a substituted hydroxyl group and the hydroxyl was substituted with a $C_1$ alkyl group then the resultant compound would be anisole ($C_6H_5OCH_3$).

Substituent groups amenable herein include without limitation, halogen, hydroxyl, alkyl, alkenyl, alkynyl, acyl (—C (O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N ($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)—N($R_{bb}$) ($R_{cc}$)), thioureido (—N($R_{bb}$)C(S)N($R_{bb}$)($R_{cc}$)), guanidinyl (—N($R_{bb}$)C(=$NR_{bb}$)N($R_{bb}$)($R_{cc}$)), amidinyl (—C(=$NR_{bb}$) N($R_{bb}$)($R_{cc}$) or —N($R_{bb}$)C(=$NR_{bb}$)($R_{aa}$)), thiol (—$SR_{bb}$), sulfinyl (—S(O)$R_{bb}$), sulfonyl (—S(O)$_2R_{bb}$) and sulfonimidoyl (—S(O)$_2$N($R_{bb}$)($R_{cc}$) or —N($R_{bb}$)S(O)$_2R_{bb}$). Wherein each $R_{aa}$, $R_{bb}$ and $R_{cc}$ is, independently, H, an optionally linked chemical functional group or a further substituent group with a preferred list including without limitation, H, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein the term "nucleobase" generally refers to the nucleobase of a nucleoside or modified nucleoside (sometimes referred to simply as the base in the context of a nucleoside). The term "heterocyclic base moiety" is broader than the term nucleobase in that it includes any heterocyclic base that can be attached to a sugar or sugar surrogate group to prepare a nucleoside or modified nucleoside. In one embodiment, a heterocyclic base moiety is any heterocyclic system that contains one or more atoms or groups of atoms capable of hydrogen bonding to a heterocyclic base of a nucleic acid. In certain embodiments, nucleobase refers to purines, modified purines, pyrimidines and modified pyrimidines. Such heterocyclic base moieties include but are not limited to naturally occurring nucleobases (adenine, guanine, thymine, cytosine and uracil) and protected forms of unmodified nucleobases (4-N-benzoylcytosine, 6-N-benzoyladenine and 2-N-isobutyrylguanine) as well as modified (5-methyl cytosine) or non-naturally occurring heterocyclic base moieties and synthetic mimetics thereof (such as for example phenoxazines). In certain embodiments, each heterocyclic base moiety is, independently, uracil, thymine, cytosine, 4-N-benzoylcytosine, 5-methylcytosine, 4-N-benzoyl-5-methylcytosine, adenine, 6-N-benzoyladenine, guanine or 2-N-isobutyrylguanine. In certain embodiments, each heterocyclic base moiety is, independently, uracil, thymine, cytosine, 5-methylcytosine, adenine, 6-N-benzoyladenine or guanine.

In certain embodiments, heterocyclic base moieties include without limitation modified nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—CC≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein.

As used herein the term "sugar moiety" refers to naturally occurring sugars having a furanose ring system (ribose and 2'-deoxyribose), synthetic and/or non-naturally occurring sugars having a modified furanose ring system and sugar surrogates wherein the furanose ring has been replaced with a mono or polycyclic ring system such as for example a morpholino or hexitol ring system or a non-cyclic sugar surrogate such as that used in peptide nucleic acids. The sugar moiety of a monomer subunit provides the reactive groups that enable the linking of adjacent monomer subunits into an oligomeric compound. Illustrative examples of sugar moieties useful in the preparation of oligomeric compounds include without limitation, β-D-ribose, β-D-2'-deoxyribose, substituted sugars (such as 2', 5' and bis substituted sugars), 4'-S-sugars (such as 4'-S-ribose, 4'-S-2'-deoxyribose and 4'-S-2'-substituted ribose wherein the ring oxygen atom has been replaced with a sulfur atom), bicyclic modified sugars (such as the 2'-O—CH(CH$_3$)-4', 2'-O—CH$_2$-4' or 2'-O—(CH$_2$)$_2$-4' bridged ribose derived bicyclic sugars) and sugar surrogates (such as for example when the ribose ring has been replaced with a morpholino, a hexitol ring system or an open non-cyclic system).

As used herein the term "sugar surrogate" refers to replacement of the nucleoside furanose ring with a non-furanose (or 4'-substituted furanose) group with another structure such as another ring system or open system. Such structures can be as simple as a six membered ring as opposed to the five membered furanose ring or can be more complicated such as a bicyclic or tricyclic ring system or a non-ring system such as that used in peptide nucleic acid. In certain embodiments, sugar surrogates include without limitation sugar surrogate groups such as morpholinos, cyclohexenyls and cyclohexitols. In general the heterocyclic base is maintained even when the sugar moiety is a sugar surrogate so that the resulting monomer subunit will be able to hybridize.

As used herein the term "sugar substituent group" refers to a group that is covalently attached to a sugar moiety. In certain embodiments, examples of sugar substituent groups include without limitation halogen, alkyl, substituted alkyl, alkoxy, substituted alkoxy, alkenyl, substituted alkenyl, alkynyl, substituted alkynyl, amino, substituted amino, thio, substituted thio and azido. In certain embodiments the alkyl and alkoxy groups are $C_1$ to $C_6$. In certain embodiments, the alkenyl and alkynyl groups are $C_2$ to $C_6$. In certain embodiments, examples of sugar substituent groups include without limitation 2'-F, 2'-allyl, 2'-amino, 2'-azido, 2'-thio, 2'-O-allyl, 2'-OCF$_3$, 2'-O—C$_1$-C$_{10}$ alkyl, 2'-OCH$_3$, 2'-O(CH$_2$)$_n$CH$_3$, 2'-OCH$_2$CH$_3$, 2'-O—(CH$_2$)$_2$CH$_3$, 2'-O—(CH$_2$)$_2$—O—CH$_3$ (MOE), 2'-O[(CH$_2$)$_n$O]$_m$CH$_3$, 2'-O(CH$_2$)$_2$SCH$_3$, 2'-O—(CH$_2$)$_3$—N(R$_p$)(R$_q$), 2'-O(CH$_2$)$_n$NH$_2$, 2'-O—(CH$_2$)$_2$—O—N(R$_p$)(R$_q$), O(CH$_2$)$_n$ON[(CH$_2$)$_n$CH$_3$]$_2$, 2'-O(CH$_2$)$_n$ONH$_2$, 2'-O—(CH$_2$)$_2$—O—(CH$_2$)$_2$—N(R$_p$)(R$_q$), 2'-O—CH$_2$C(=O)—N(R$_p$)(R$_q$), 2'-OCH$_2$C(=O)N(H)CH$_3$, 2'-O—CH$_2$C(=O)—N(H)—(CH$_2$)$_2$—N(R$_p$)(R$_q$) and 2'-O—CH$_2$—N(H)—C(=NR$_r$)[N(R$_p$)(R$_q$)], wherein each R$_p$, R$_q$ and R$_r$ is, independently, H, substituted or unsubstituted C$_1$-C$_{10}$ alkyl or a protecting group and where n and m are from 1 to about 10.

As used herein the term "monomer subunit" is meant to include all manner of monomers that are amenable to oligomer synthesis. In general a monomer subunit includes at least a sugar moiety having at least two reactive sites that can form linkages to further monomer subunits. Essentially all monomer subunits include a heterocyclic base moiety that is hybridizable to a complementary site on a nucleic acid target. Reactive sites on monomer subunits located on the termini of an oligomeric compound can be protected or unprotected (generally OH) or can form an attachment to a terminal group (conjugate or other group). Monomer subunits include, without limitation, nucleosides and modified nucleosides. In certain embodiments, monomer subunits include nucleosides such as β-D-ribonucleosides and β-D-2'-deoxyribnucleosides and modified nucleosides including but not limited to substituted nucleosides (such as 2', 5' and bis substituted nucleosides), 4'-S-modified nucleosides (such as 4'-S-ribonucleosides, 4'-S-2'-deoxyribonucleosides and 4'-S-2'-substituted ribonucleosides), bicyclic modified nucleosides (such as bicyclic nucleosides wherein the sugar moiety has a 2'-O—CHR$_a$-4' bridging group, wherein R$_a$ is H, alkyl or substituted alkyl), other modified nucleosides and nucleosides having sugar surrogates.

As used herein, the term "nucleoside" refers to a nucleobase-sugar combination. The two most common classes of such nucleobases are purines and pyrimidines. The term nucleoside includes β-D-ribonucleosides and β-D-2'-deoxyribonucleosides.

As used herein, the term "nucleotide" refers to a nucleoside further comprising a modified or unmodified phosphate internucleoside linking group or a non-phosphate internucleoside linking group. For nucleotides that include a pentofuranosyl sugar, the internucleoside linking group can be linked to either the 2', 3' or 5' hydroxyl moiety of the sugar. The phosphate and or a non-phosphate internucleoside linking groups are routinely used to covalently link adjacent nucleosides to one another to form a linear polymeric compound.

As used herein the term "modified nucleoside" refers to a nucleoside comprising a modified heterocyclic base and or a sugar moiety other than ribose and 2'-deoxyribose. In certain embodiments, a modified nucleoside comprises a modified heterocyclic base moiety. In certain embodiments, a modified nucleoside comprises a sugar moiety other than ribose and 2'-deoxyribose. In certain embodiments, a modified nucleoside comprises a modified heterocyclic base moiety and a sugar moiety other than ribose and 2'-deoxyribose. The term "modified nucleoside" is intended to include all manner of modified nucleosides that can be incorporated into an oligomeric compound using standard oligomer synthesis protocols. Modified nucleosides include abasic nucleosides but in general a heterocyclic base moiety is included for hybridization to a complementary nucleic acid target.

In certain embodiments, modified nucleosides include a furanose ring system or a modified furanose ring system. Modified furanose ring systems include 4'-S analogs, one or more substitutions at any position such as for example the 2', 3', 4' and 5' positions and addition of bridges for form additional rings such as a 2'-O—CH(CH$_3$)-4' bridge. Such modified nucleosides include without limitation, substituted nucleosides (such as 2', 5', and/or 4' substituted nucleosides) 4'-S-modified nucleosides, (such as 4'-S-ribonucleosides, 4'-S-2'-deoxyribonucleosides and 4'-S-2'-substituted ribonucleosides), bicyclic modified nucleosides (such as 2'-O—CH(CH$_3$)-4', 2'-O—CH$_2$-4' or 2'-O—(CH$_2$)$_2$-4' bridged furanose analogs) and base modified nucleosides. The sugar can be modified with more than one of these modifications listed such as for example a bicyclic modified nucleoside further including a 5'-substitution or a 5' or 4' substituted nucleoside further including a 2' substituent. The term modified nucleoside also includes combinations of these modifications such as base and sugar modified nucleosides. These modifications are meant to be illustrative and not exhaustive as other modifications are known in the art and are also envisioned as possible modifications for the modified nucleosides described herein.

In certain embodiments, modified nucleosides comprise a sugar surrogate wherein the furanose ring has been replaced with a mono or polycyclic ring system or a non-cyclic sugar surrogate such as that used in peptide nucleic acids. Illustrative examples of sugar moieties for such modified nucleosides includes without limitation morpholino, hexitol, cyclohexenyl, 2.2.2 and 3.2.1 cyclohexose and open non-cyclic groups.

In certain embodiments, modified nucleosides comprise a non-naturally occurring sugar moiety and a modified heterocyclic base moiety. Such modified nucleosides include without limitation modified nucleosides wherein the heterocyclic base moiety is replaced with a phenoxazine moiety (for example the 9-(2-aminoethoxy)-1,3-diazaphenoxazine-2-one group, also referred to as a G-clamp which forms four hydrogen bonds when hybridized with a guanosine base) and further replacement of the sugar moiety with a sugar surrogate group such as for example a morpholino, a cyclohexenyl or a bicyclo[3.1.0]hexyl.

As used herein the term "bicyclic nucleoside" refers to a nucleoside comprising at least a bicyclic sugar moiety. Examples of bicyclic nucleosides include without limitation nucleosides having a furanosyl sugar that comprises a bridge between two of the non-geminal carbons atoms. In certain embodiments, bicyclic nucleosides have a bridge between the 4' and 2' carbon atoms.

Examples of such 4' to 2' bridged bicyclic nucleosides, include but are not limited to one of formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-C—H(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO2008/150729, published Dec. 11, 2008); 4'-CH$_2$—O—N(CH$_3$)-2' (see U.S. Pat. No. 7,96,345, issued on Apr. 13, 2010); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya, et al., J. Org. Chem., 2009, 74, 118-134); and 4'-CH$_2$—CH$_2$-2' and 4'-CH$_2$—C—(=CH$_2$)-2' (and analogs thereof see published International Application WO 2008/154401, published on Dec. 8, 2008). Further bicyclic nucleosides have been reported in published literature (see for example: Srivastava et al., J. Am. Chem. Soc., 2007, 129(26) 8362-8379; Frieden et al., Nucleic Acids Research, 2003, 21, 6365-6372; Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; Wahlestedt et al., Proc. Natl. Acad. Sci. U.S.A., 2000, 97, 5633-5638; Singh et al., Chem. Commun., 1998, 4, 455-456; Koshkin et al., Tetrahedron, 1998, 54, 3607-3630; Kumar et al., Bioorg. Med. Chem. Lett., 1998, 8, 2219-2222; Singh et al., J. Org. Chem., 1998, 63, 10035-10039; U.S. Pat. Nos. 7,741,457; 7,696,345; 7,547,684; 7,399,845; 7,053,207; 7,034,133; 6,794,499; 6,770,748; 6,670,461; 6,525,191; 6,268,490; U.S. Patent Publication Nos.: US2008-0039618; U.S. Patent Applications, Ser. Nos. 61/099,844; 61/097,787; 61/086,231; 61/056,564; 61/026,998; 61/026,995; 60/989,574; International applications WO2009/006478; WO2008/154401; WO2008/150729; WO 2007/134181; WO 2005/021570; WO 2004/106356; WO 94/14226). Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

Some representative U.S. patents that teach the preparation of such modified sugars include without limitation, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,670,633; 5,700,920; 5,792,847 and 6,600,032 and International Application PCT/US2005/019219, filed Jun. 2, 2005 and published as WO 2005/121371 on Dec. 22, 2005 certain of which are commonly owned with the instant application, and each of which is herein incorporated by reference in its entirety.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

The term "oligonucleoside" refers to a sequence of nucleosides that are joined by internucleoside linkages that do not have phosphorus atoms. Internucleoside linkages of this type include short chain alkyl, cycloalkyl, mixed heteroatom alkyl, mixed heteroatom cycloalkyl, one or more short chain heteroatomic and one or more short chain heterocyclic. These internucleoside linkages include without limitation, siloxane, sulfide, sulfoxide, sulfone, acetyl, formacetyl, thioformacetyl, methylene formacetyl, thioformacetyl, alkenyl, sulfamate, methyleneimino, methylenehydrazino, sulfonate, sulfonamide, amide and others having mixed N, O, S and CH$_2$ component parts.

As used herein, the term "oligomeric compound" refers to a contiguous sequence of linked monomer subunits. Each linked monomer subunit normally includes a heterocyclic base moiety but monomer subunits also include those without a heterocyclic base moiety such as abasic monomer subunits. In certain embodiments, at least some and generally most if not essentially all of the heterocyclic bases in an oligomeric compound are capable of hybridizing to a nucleic acid molecule, normally a preselected RNA target. The term "oligomeric compound" therefore includes oligonucleotides, oligonucleotide analogs and oligonucleosides. It also includes polymers having one or a plurality of nucleosides having sugar surrogate groups.

In certain embodiments, oligomeric compounds comprise a plurality of monomer subunits independently selected from naturally occurring nucleosides, non-naturally occurring nucleosides, modified nucleosides and nucleosides having sugar surrogate groups. In certain embodiments, oligomeric compounds are single stranded. In certain embodiments, oligomeric compounds are double stranded comprising a double-stranded duplex. In certain embodiments, oligomeric compounds comprise one or more conjugate groups and/or terminal groups.

As used herein, "antisense compound" refers to an oligomeric compound, at least a portion of which is at least partially complementary to a target nucleic acid to which it hybridizes. In certain embodiments, an antisense compound modulates (increases or decreases) expression or amount of a target nucleic acid. In certain embodiments, an antisense compound alters splicing of a target pre-mRNA resulting in a different splice variant. In certain embodiments, an antisense compound modulates expression of one or more different target proteins. Antisense mechanisms contemplated herein include, but are not limited to an RNase H mechanism, RNAi mechanisms, splicing modulation, translational arrest, altering RNA processing, inhibiting microRNA function, or mimicking microRNA function.

As used herein the term "internucleoside linkage" or "internucleoside linking group" is meant to include all manner of internucleoside linking groups known in the art including but not limited to, phosphorus containing internucleoside linking groups such as phosphodiester and phosphorothioate, and non-phosphorus containing internucleoside linking groups such as formacetyl and methyleneimino. Internucleoside linkages also includes neutral non-ionic internucleoside linkages such as amide-3 (3'-$CH_2$—C(=O)—N(H)-5'), amide-4 (3'-$CH_2$—N(H)—C(=O)-5') and methylphosphonate wherein a phosphorus atom is not always present. In certain embodiments, each internucleoside linkage is, independently, a phosphorothioate or a phosphodiester internucleoside linkage. In certain embodiments, essentially each internucleoside linkage is a phosphodiester internucleoside linkage. In certain embodiments, essentially each internucleoside linkage is, a phosphorothioate internucleoside linkage.

In certain embodiments, oligomeric compounds as provided herein can be prepared having one or more internucleoside linkages containing modified e.g. non-naturally occurring internucleoside linkages. The two main classes of internucleoside linkages are defined by the presence or absence of a phosphorus atom. Modified internucleoside linkages having a phosphorus atom include without limitation, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Oligonucleotides having inverted polarity can comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative U.S. patents that teach the preparation of the above phosphorus containing linkages include without limitation, U.S. Pat. Nos. 3,687,808; 4,469,863; 4,476,301; 5,023,243; 5,177,196; 5,188,897; 5,194,599; 5,264,423; 5,276,019; 5,278,302; 5,286,717; 5,321,131; 5,399,676; 5,405,939; 5,453,496; 5,455,233; 5,466,677; 5,476,925; 5,519,126; 5,527,899; 5,536,821; 5,541,306; 5,550,111; 5,563,253; 5,565,555; 5,571,799; 5,587,361; 5,625,050; 5,672,697 and 5,721,218, certain of which are commonly owned with this application, and each of which is herein incorporated by reference.

In certain embodiments, oligomeric compounds as provided herein can be prepared having one or more non-phosphorus containing internucleoside linkages. Such oligomeric compounds include without limitation, those that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include without limitation, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; 5,677,439; 5,646,269 and 5,792,608, certain of which are commonly owned with this application, and each of which is herein incorporated by reference.

As used herein "neutral internucleoside linkage" is intended to include internucleoside linkages that are non-ionic. Neutral internucleoside linkages include without limitation, phosphotriesters, methylphosphonates, MMI (3'-$CH_2$—N($CH_3$)—O-5'), amide-3 (3'-$CH_2$—C(=O)—N(H)-5), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, oligomeric compounds as provided herein can be prepared having one or more optionally protected phosphorus containing internucleoside linkages. Representative protecting groups for phosphorus containing internucleoside linkages such as phosphodiester and phosphorothioate linkages include β-cyanoethyl, diphenylsilylethyl, δ-cyanobutenyl, cyano p-xylyl (CPX), N-methyl-N-trifluoroacetyl ethyl (META), acetoxy phenoxy ethyl (APE) and butene-4-yl groups. See for example U.S. Pat. Nos. 4,725,677 and Re. 34,069 (β-cyanoethyl); Beaucage et al., *Tetrahedron*, 1993, 49(10), 1925-1963; Beaucage et al., *Tetrahedron*, 1993, 49(46), 10441-10488; Beaucage et al., *Tetrahedron*, 1992, 48(12), 2223-2311.

As used herein, "complementarity" in reference to nucleobases refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases or more broadly, heterocyclic base moieties, comprising certain modifications may maintain the ability to pair with a counterpart nucleobase and thus, are still capable of complementarity.

As used herein, "non-complementary" "in reference to nucleobases refers to a pair of nucleobases that do not form hydrogen bonds with one another or otherwise support hybridization.

As used herein, "hybridization" refers to the pairing of complementary oligomeric compounds (e.g., an antisense compound and its target nucleic acid). While not wanting to be limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, "target nucleic acid" refers to any nucleic acid molecule the expression, amount, or activity of which is capable of being modulated by an antisense compound. In certain embodiments, the target nucleic acid is DNA or RNA. In certain embodiments, the target RNA is mRNA, pre-mRNA, non-coding RNA, pri-microRNA, pre-microRNA, mature microRNA, promoter-directed RNA, or natural antisense transcripts. For example, the target nucleic acid can be a cellular gene (or mRNA transcribed from the gene) whose expression is associated with a particular disorder or disease state, or a nucleic acid molecule from an infectious agent. In certain embodiments, target nucleic acid is a viral or bacterial nucleic acid.

In certain embodiments, the preparation of oligomeric compounds as disclosed herein is performed according to literature procedures for DNA: Protocols for Oligonucleotides and Analogs, Agrawal, Ed., Humana Press, 1993, and/or RNA: Scaringe, *Methods*, 2001, 23, 206-217; Gait et al., *Applications of Chemically synthesized RNA in RNA: Protein Interactions*, Smith, Ed., 1998, 1-36; Gallo et al., *Tetrahedron*, 2001, 57, 5707-5713. Additional methods for solid-phase synthesis may be found in Caruthers U.S. Pat. Nos. 4,415,732; 4,458,066; 4,500,707; 4,668,777; 4,973,679; and 5,132,418; and Koster U.S. Pat. Nos. 4,725,677 and Re. 34,069.

Oligomeric compounds are routinely prepared using solid support methods as opposed to solution phase methods. Commercially available equipment commonly used for the preparation of oligomeric compounds that utilize the solid support method is sold by several vendors including, for example, Applied Biosystems (Foster City, Calif.). Any other means for such synthesis known in the art may additionally or alternatively be employed. Suitable solid phase techniques, including automated synthesis techniques, are described in *Oligonucleotides and Analogues, a Practical Approach*, F. Eckstein, Ed., Oxford University Press, New York, 1991.

The synthesis of RNA and related analogs relative to the synthesis of DNA and related analogs has been increasing as efforts in RNA interference and micro RNA increase. The primary RNA synthesis strategies that are presently being used commercially include 5'-O-DMT-2'-O-t-butyldimethylsilyl (TBDMS), 5'-O-DMT-2'-O-[1(2-fluorophenyl)-4-methoxypiperidin-4-yl] (FPMP), 2'-O-[(triisopropylsilyl)oxy]methyl (2'-O—CH$_2$—O—Si(iPr)$_3$ (TOM) and the 5'-O-silyl ether-2'-ACE (5'-O-bis(trimethylsiloxy)cyclododecyloxysilyl ether (DOD)-2'-O-bis(2-acetoxyethoxy)methyl (ACE). A current list of some of the major companies currently offering RNA products include Pierce Nucleic Acid Technologies, Dharmacon Research Inc., Ameri Biotechnologies Inc., and Integrated DNA Technologies, Inc. One company, Princeton Separations, is marketing an RNA synthesis activator advertised to reduce coupling times especially with TOM and TBDMS chemistries. The primary groups being used for commercial RNA synthesis are: TBDMS: 5'-O-DMT-2'-O-t-butyldimethylsilyl; TOM: 2'-O-[(triisopropylsilyl)oxy]methyl; DOD/ACE: (5'-O-bis(trimethylsiloxy)cyclododecyloxysilyl ether-2'-O-bis(2-acetoxyethoxy)methyl; and FPMP: 5'-O-DMT-2'-O-[1 (2-fluorophenyl)-4-ethoxypiperidin-4-yl]. In certain embodiments, each of the aforementioned RNA synthesis strategies can be used herein. In certain embodiments, the aforementioned RNA synthesis strategies can be performed together in a hybrid fashion e.g. using a 5'-protecting group from one strategy with a 2'-O-protecting from another strategy.

In certain embodiments, methods of synthesizing of oligomeric compounds are provided that utilize support medium. In certain embodiments, reactive groups on the support medium are first functionalized with Unylinker™ linking groups prior to addition of the first monomer subunit. A first monomer subunit is attached to a support medium with subsequent monomer subunits iteratively coupled to provide a desired oligomeric compound. The industry standard for large scale oligomeric compound synthesis uses solid support media in a reaction vessel. The growing oligomeric compound is reacted and washed with various reagents and solvents while attached to the solid support. In certain embodiments, support media can be selected having variable solubility in different solvents to allow the growing support bound oligomeric compound to be either in or out of solution at various points in the synthesis process as desired. In certain embodiments, soluble supports include soluble polymer supports that allow precipitating and dissolving the iteratively synthesized product at desired points in the synthesis (Gravert et al., Chem. Rev., 1997, 97, 489-510).

All documents, or portions of documents, cited in this application, including, but not limited to, patents, patent applications, articles, books, and treatises, are hereby expressly incorporated by reference in their entirety for any purpose.

Those skilled in the art, having possession of the present disclosure will be able to prepare oligomeric compounds, comprising a contiguous sequence of linked monomer subunits, of essentially any viable length. While in certain embodiments, oligomeric compounds provided herein can be prepared as described, the following examples serve only to illustrate and are not intended to be limiting.

Example 1

Preparation of Compound 2

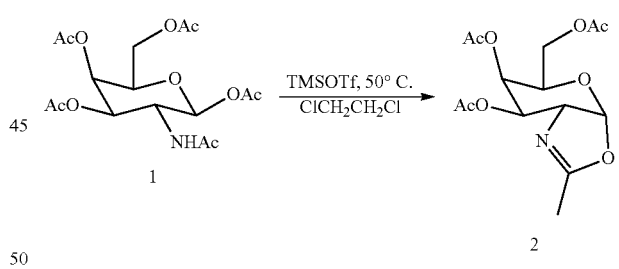

Compound 1 (2-acetamido-1,3,4,6-tetra-O-acetyl-2-deoxy-β-D-galactopyranose or galactosamine pentaacetate) is commercially available. Following a published procedure, Compound 2 was obtained in a 93% yield (Rensen et al., *J. Med. Chem.*, 2004, 47, 5798-5808; Nakabayashi et al., Carbohyrate Res., 1986, 150, C7).

Example 2

Preparation of Compound 5

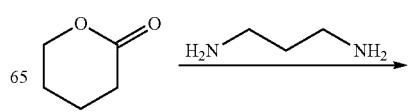

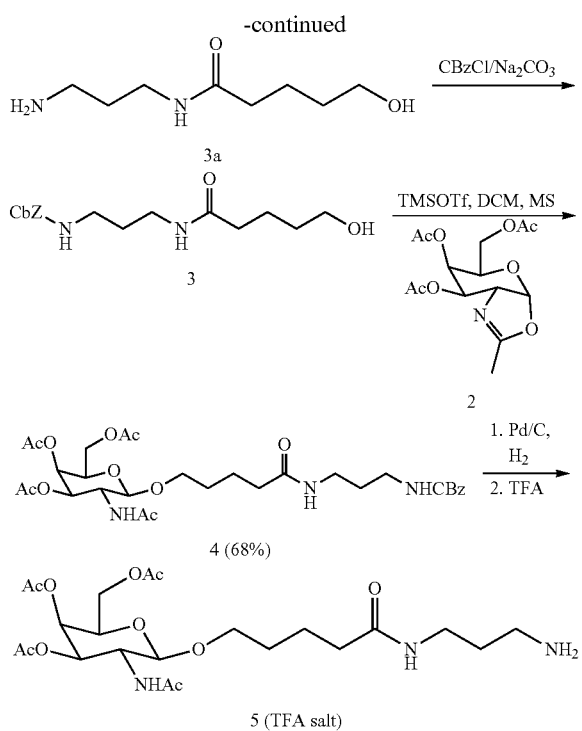

Delta-valerolactone (46.3 mL, 499.4 mmol, commercially available) was added to 1,3-diaminopropane (148 mL, 1773 mmol, commercially available) in a round bottom flask. The reaction was vigorously stirred. The clear solution obtained was stirred at room temperature for 12 hours and monitored by LCMS. The reaction mixture was concentrated under reduced pressure to provide the crude intermediate Compound 3a (94 g) which was used for the next step without purification. The structure of the crude amide intermediate compound (Compound 3a) was confirmed by LCMS and $^1$H NMR.

The crude amide intermediate compound (Compound 3a) from above (94 g, 499.42 mmol) and sodium carbonate (80 g, 749.1 mmol) were suspended in a mixture of 1,4-dioxane (900 mL) and water (180 mL) and benzyl chloroformate (106 mL, 749.1 mmol) was added. The reaction mixture was stirred at room temperature for 12 hours and then analyzed by LCMS. The reaction was partitioned with ethyl acetate and water. The organic layer was separated and the aqueous layer was extracted with ethyl acetate twice. The ethyl acetate layers were combined and concentrated. The residue was suspended in water (900 mL) and extracted with dichloromethane/5% MeOH (450 mL three times). The dichloromethane layers were combined, dried over sodium sulfate and concentrated to thick white slurry. The crude material was crystallized with acetone/hexanes to provide Compound 3 as white solid (119.64 g, 78% in these two steps). The structure of Compound 3 was confirmed by LCMS and $^1$H NMR.

Compound 2 (17.2 g, 52.2 mmol), Compound 3 (16.11 g, 52.2 mmol) and pre-dried molecular sieves (20 g) were suspended in dry dichloromethane (120 mL). The mixture was stirred at room temperature for 30 minutes and TMSOTf (4.7 mL) was added. The reaction was stirred at room temperature for 12 hours and then analyzed by LCMS. The reaction mixture was poured into icy NaHCO$_3$ and extracted with dichloromethane. The dichloromethane extract was washed with brine and concentrated to dryness. The crude product was purified via Biotage silica gel column that was eluted with 2%, (5 column volumes "CV"), 3% (3 CV), 5% (4 CV) and 8% (3 CV) MeOH in dichloromethane to provide Compound 4 as a white foam (22.8 g, 68%). The structure of Compound 4 was confirmed by LCMS and $^1$H NMR.

Compound 4 (5.6 g) was dissolved in ethyl acetate (40 mL) and methanol (40 mL) and palladium on carbon (0.93 g, wet) was added. The reaction was stirred under hydrogen at room temperature for 12 hours and then analyzed by LCMS. The reaction was filtered through a celite pad. The celite pad was thoroughly washed with a mixture of ethyl acetate and methanol (50 mL each). The wash filtrate and filtered residue were combined, TFA (0.67 mL) was added, then the solvent was removed under reduced pressure. The residue was co-evaporated with toluene (2×30 mL) to dryness to provide Compound 5 (TFA salt) as a yellow foam (5.42 g, quantitative). The structure of Compound 5 was confirmed by LCMS.

Example 3

Preparation of Compound 7

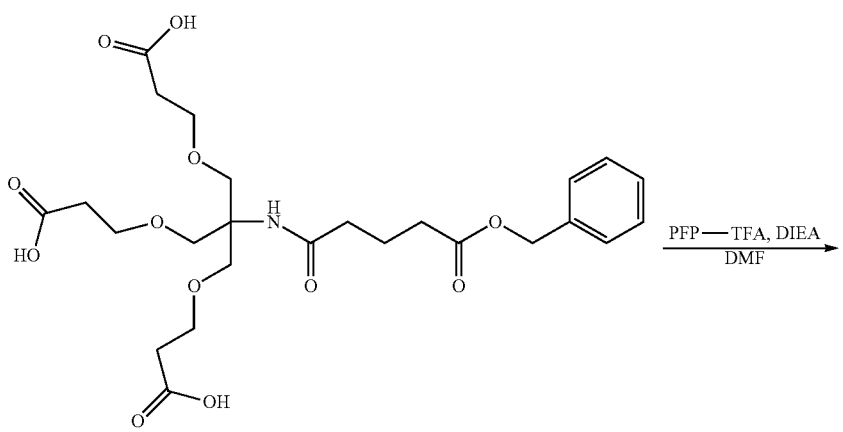

6

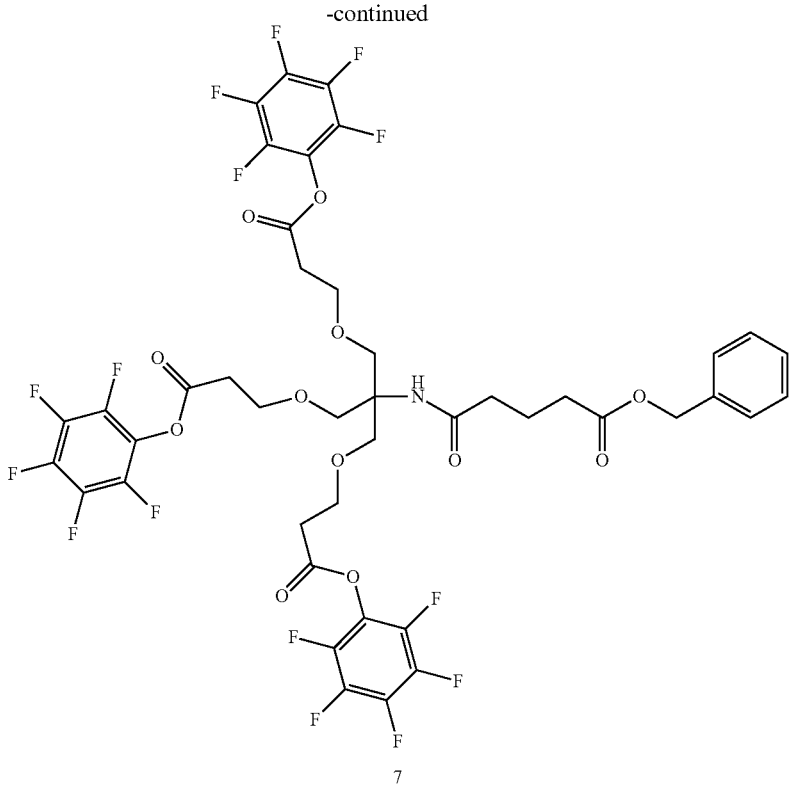

7

Compound 6 (20 g, commercially available) was dissolved in DMF (150 mL) and DIEA (51 mL) was added. To this mixture, pentafluorophenyl trifluoroacetate (25.4 mL, PFP-TFA) was slowly introduced. The color of the reaction went from colorless to burgundy. The reaction was stirred at RT overnight and monitored by LCMS. The reaction was treated with 1 N NaHSO₄ (500 mL) and extracted with ethyl acetate (600 mL). The ethyl acetate extract was washed with brine (150 mL×2), sat. NaHCO₃ (200 mL×2), brine (150 mL×2) and dried over Na₂SO₄. The ethyl acetate was concentrated to dryness and purified via Biotage (340 g) silica gel column eluted with 10% (3 CV), 20% (3 CV), 30% (6 CV) ethyl acetate in Hexanes to provide Compound 7 as an orange oil (31.87 g, 83%). The structure of Compound 7 was confirmed by LCMS and $^1$H NMR.

Alternate Method for the Preparation of Compound 7

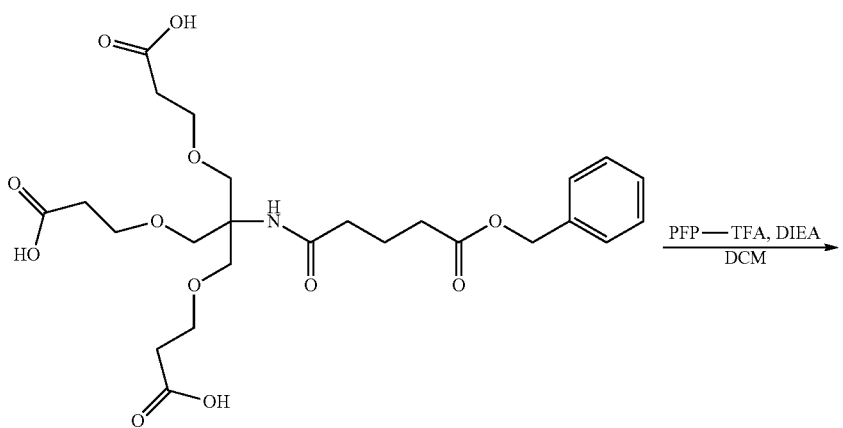

6

-continued

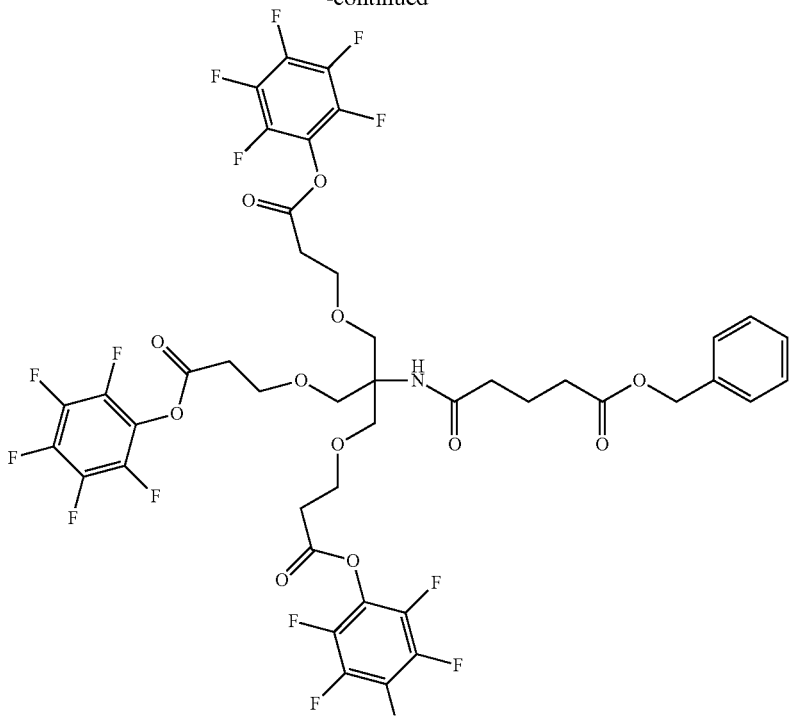

7

Compound 6 (commercially available from TCI Scientific, Edmonton, A B, Canada, product #TCS083008) was initially recrystallized as the purity was assayed to be only at about 70%. Purification of Compound 6 provided much purer Compound 7. Note: recrystallization is not required for lots already at about 95% purity. Compound 6 (148.56 grams) was suspended in dry ACN (625 mL) with stirring and heating to 40° C. until all solids dissolved. The reaction was allowed to cool to room temp slowly and then cooled in a refrigerator at 4° C. for one hour. Over the next 30 minutes, a white solid precipitated. The resulting slurry was diluted with cold ACN (250 mL), and was chilled in a salted ice bath (−2° C.) for 1 hour. The mixture was filtered and the solid filtrate rinsed with cold ACN (200 mL) and cold methyl tertiary butyl ether (MTBE, 400 mL) to provide Compound 6 (102 grams, 69% recovery, at 97% purity).

Purified Compound 6 (50 g, 91 mmol) was suspended in dry DCM (425 mL). The reaction mixture was cooled in an ice bath and diisopropylethylamine (DIEA) was added (120 mL, 730 mmol, 8 eq.), and the reaction was purged with nitrogen. PFP-TFA (53.5 mL, 311 mmol, 3.4 eq.) was added slowly to the reaction mixture via addition funnel (~3.5 mL/min). The color of the reaction changed from colorless to light pink and gave off a light smoke which was blown away with a stream of nitrogen. After the addition was complete, the reaction was stirred on ice for 15 minutes, then at room temperature for 1 hour. Over the course of the reaction the color changed to burgundy and then to dark orange. The reaction was monitored by TLC (7:3 hexanes/EtOAc) and LCMS.

At completion ice water (400 mL) and saturated aqueous NaHCO$_3$(100 mL) was added. The reaction mixture was stirred vigorously, and was transferred to a separatory funnel. The organic layer was recovered and washed with water (2×500 mL), then with brine (1×500 mL). The organics were dried over MgSO$_4$, filtered, and concentrated under reduced pressure to a dark orange oil to provide the crude product (72.0 g). The crude product was diluted with DCM (~100 mL), and was passed through a pad of silica gel (600 mL fritted funnel, 4" wide, 2.5" thick). The product was eluted with DCM (~500 mL). The majority of the orange color was trapped by the silica gel. The filtrate was concentrated under reduced pressure to give Compound 7 (89 g, 93%) as a dark orange syrup. The structure of Compound 7 was confirmed by LCMS, $^1$H NMR and $^{19}$F NMR.

Example 4

Preparation of Compound 8a

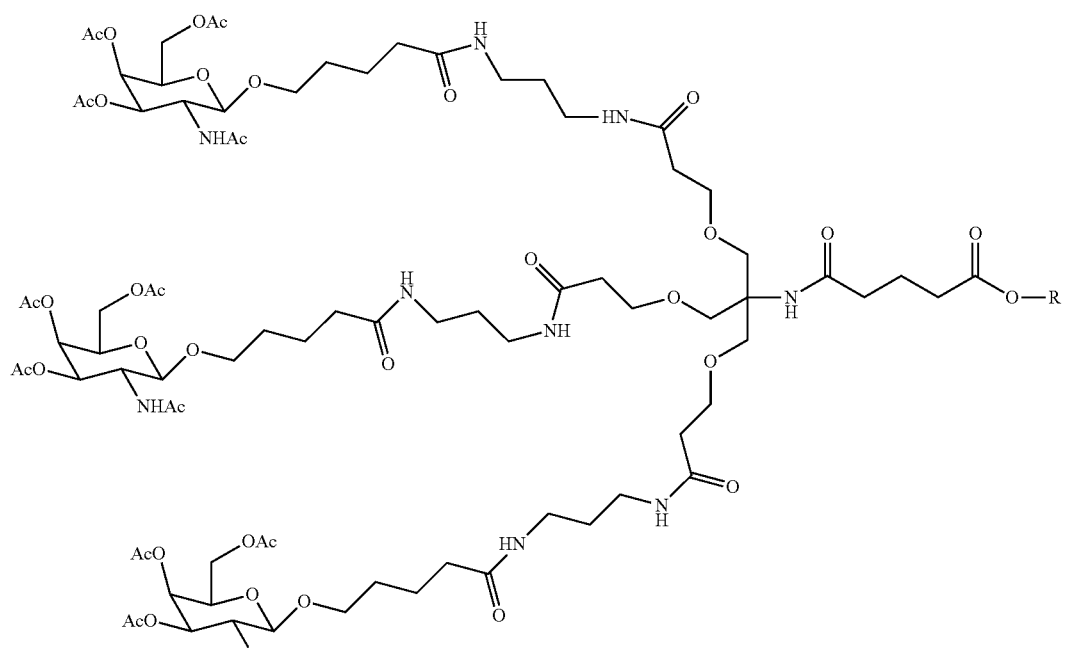

Compound 8a, R = benzyl

Compound 5 (5.35 g, TFA salt) and Compound 7 (2.5 g) were dissolved in acetonitrile (20 mL) and DIEA (2.5 mL) was added (color changed from yellow to light brown). The reaction mixture was stirred at room temperature and monitored by LCMS (reaction was done in 20 minutes). The reaction mixture was diluted with dichloromethane (200 mL) and washed with 10% aqueous ammonium chloride solution (100 mL), brine (100 mL), and dried over $Na_2SO_4$. The organic phase was concentrated under reduced pressure to yield crude product (5.58 g, 90%) as light yellow foam. Compound 8a was confirmed by LCMS and $^1H$ NMR.

Example 5

Preparation of Compound 8c

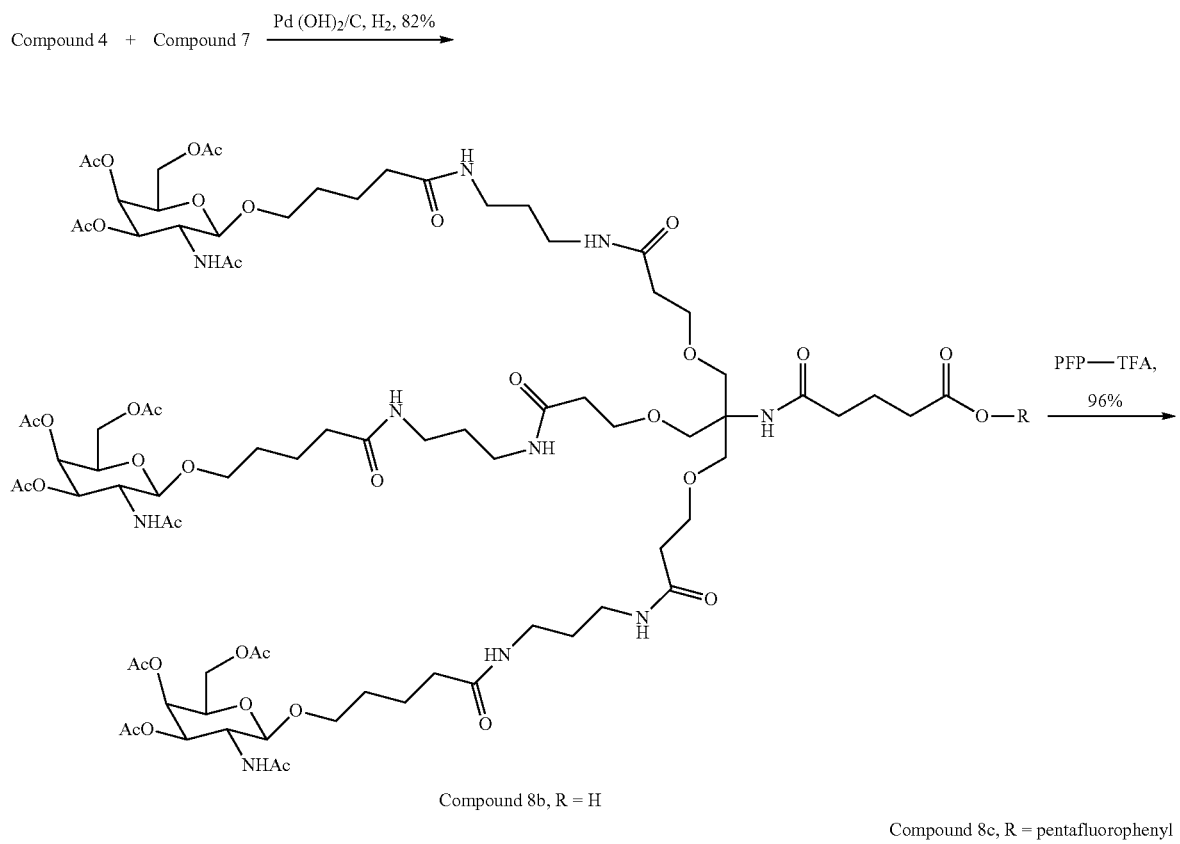

Compound 8b, R = H

Compound 8c, R = pentafluorophenyl

Compound 4 (10.24 g, 16.1 mmol) and Compound 7 (5 g, 4.2 mmol) were dissolved in acetonitrile (100 mL). To this mixture, Pd(OH)$_2$/C (20 wt %, 3.0 g) was added. The reaction mixture was flushed with hydrogen gas and stirred under hydrogen atmosphere at room temperature. The progress of the reaction was monitored by LCMS and the reaction was completed after three hours. The reaction mixture was filtered through a pad of celite. The celite pad was washed thoroughly with acetonitrile. The wash filtrate and residue were combined and concentrated under reduced pressure. The residue was purified by silica gel column chromatography and eluted with 5-30% methanol in dichloromethane to yield 8b (7.43 g, 81%) The structure of Compound 8b was confirmed by LCMS and $^1$H NMR.

Compound 8b (5.2 g) and TEA (1.14 mL, 3 eq.) were dissolved in DMF (25 mL). To this PFP-TFA (0.937 mL, 2 eq.) was added (color changed from yellow to burgundy) dropwise. The reaction was completed after one hour as determined by LC MS analysis. The DMF was removed under reduced pressure at 50° C. The residue was diluted with dichloromethane and the organic phase was washed with 1N NaHSO$_4$ (80 mL), saturated aqueous sodium bicarbonate solution and brine. The organic phase was dried over Na$_2$SO$_4$, filtered and evaporated to yield 8c (5.71 g, quantitative) as a light pink foam. The structure of Compound 8c was confirmed by LCMS, $^1$H NMR and $^{19}$F NMR.

Example 6

Preparation of Compound 12

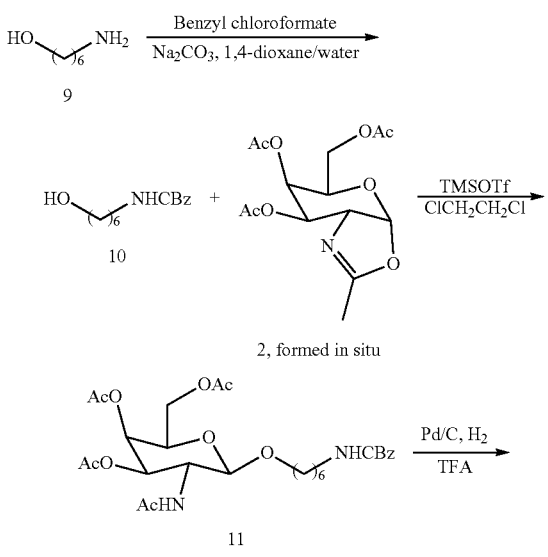

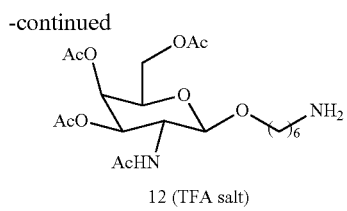

12 (TFA salt)

Aminohexanol (Compound 9, 70 g, 0.597 mol, commercially available) and $Na_2CO_3$ (110.79 g, 1.059 mol, 1.75 eq.) were added to a mixture of 1,4-dioxane (1400 mL) and water (300 mL) in a 3.0 L bottom flask equipped with mechanical stirrer and stirred for 1 hour to dissolve the salt. The resulting clear solution was cooled in an ice bath and benzyl chloroformate (178.32 g, 1.045 mol, 1.75 eq.) was added dropwise by addition funnel. The mixture was stirred overnight and allowed to warm slowly to room temperature resulting in the formation of a white precipitate. The precipitate was filtered and washed with ethyl acetate and the filtrate was extracted with ethyl acetate. The combined organic phases were washed with saturated $NaHCO_3$ (500 mL), brine (500 mL), dried over $Na_2SO_4$, filtered and the filtrate was evaporated under reduced pressure to provide a white solid. The white solid was suspended in hexanes, filtered and rinsed with fresh hexanes to provide purified Compound 10 (129.0 g, 86%). The structure of Compound 10 was confirmed by LCMS and $^1H$ NMR.

Compounds 1 and 10 were dried over $P_2O_5$ overnight under high vacuum at 35° C. in separate flasks. Compound 1 (150 g, 0.385 mol) was dissolved in anhydrous dichloroethane (500.0 mL) with stirring under nitrogen at room temperature. To the resulting clear solution was added TMSOTf (119.87 g, 0.539 mol, 1.5 eq.) with stirring for two hours to form Compound 2 in Solution 1.

Compound 10 (106.51 g, 0.424 mol, 1.1 eq.) was dissolved in anhydrous dichloroethane (1.0 L) and molecular sieves were added (powder molecular sieves ~30 g, dried at 275° C. overnight and subsequently cooled to room temperature under high vacuum) with stirring maintained for 40 minutes. To the resulting mixture was added Solution 1 by cannula dropwise slowly over a period of 1 hour with stirring for an additional 2 hours. The reaction mixture was filtered and the filtrate dripped onto an ice cold saturated solution of $NaHCO_3$ (300 mL). The organic phase was separated and washed with DI water (500 mL), brine (500 mL), dried over $Na_2SO_4$, filtered and evaporated to dryness to provide the crude material as a white solid. The crude material was suspended in EtOAc/hexanes (800 mL) and filtered to provide pure white crystalline product, Compound 11 (111.44 g). The filtrate was concentrated and the residue purified by silica gel chromatography eluted with DCM/MeOH (97/3) and the collected fractions concentrated and suspended in EtOAc/hexane (400 mL) and filtered to provide additional Compound 11 (44.0 g, for a combined yield of 70%, 155.14 g). The structure of Compound 11 was confirmed by LCMS and $^1H$ NMR.

Compound 11 (5.6 g) was dissolved in ethyl acetate (40 mL) and methanol (40 mL) and palladium on carbon (0.93 g, 10 wt % Degussa type wet) was added. The reaction mixture was stirred under hydrogen at room temperature for 12 hours and then analyzed by LCMS. The reaction was filtered through a celite pad, and the celite pad was thoroughly washed with a mixture of ethyl acetate and methanol (50 mL each). The wash filtrate and filtered residue were combined, TFA (0.74 mL) was added, then the solvent was removed under reduced pressure. The residue was co-evaporated with toluene (2×30 mL) to dryness to provide Compound 12 as a yellow foam (5.42 g, quantitative). The structure of compound 12 was confirmed by LCMS.

Example 7

Preparation of Compound 13c

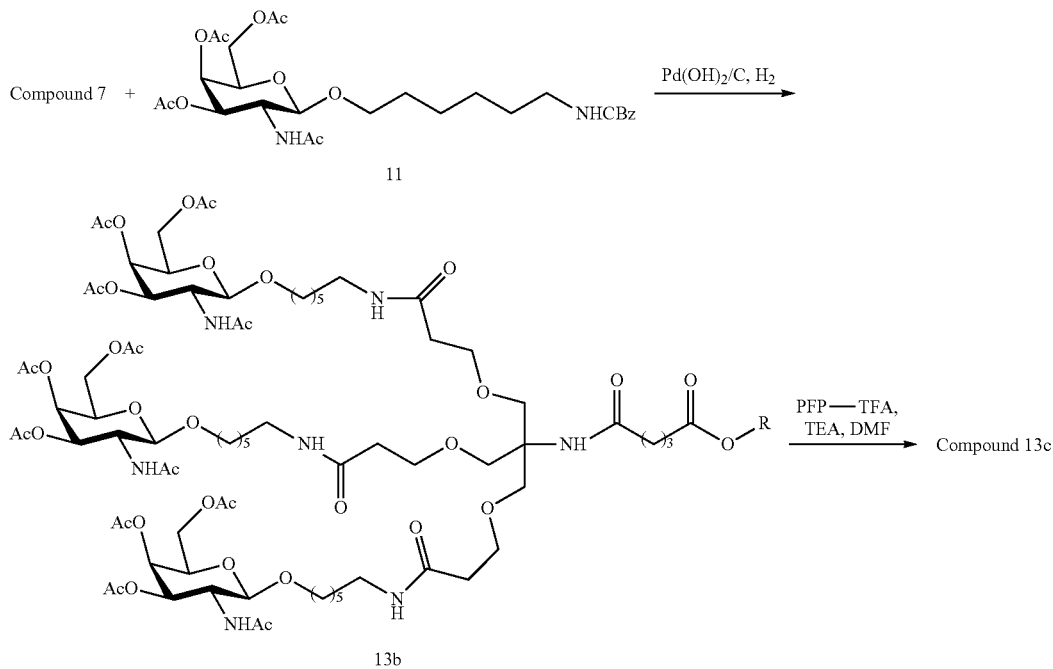

Compound 13b: R = H
Compound 13c: R = pentafluorophenyl

Compound 7 (6 g) and Compound 11 (11.39 g) were dissolved in a mixture of ethyl acetate (70 mL) and MeOH (35 mL). Pd(OH)$_2$/C (2.2 g, 20 wt %) was added and the reaction mixture was stirred at room temperature under H$_2$ with monitoring at 2 hour time points. At 12 hours the reaction was filtered and concentrated to dryness. The resulting crude product was purified via silica gel column eluted with dichloromethane (3CV), ethyl acetate (6CV), dichloromethane (3CV), 5% MeOH (6CV) and 10% MeOH (6CV) in dichloromethane to provide Compound 13b (6.9 g, 69%) as a light yellow foam. The structure of Compound 13b was confirmed by LCMS and $^1$H NMR.

Compound 13b (5.2 g) and TEA (1.14 mL, 3 eq.) were dissolved in DMF (25 mL) and PFP-TFA (0.937 mL, 2 eq.) was added. After one hour, LC MS analysis showed that the reaction was completed. The DMF was removed under reduced pressure at 50° C. The residue was diluted with dichloromethane and the solution thus obtained was washed with 1N NaHSO$_4$ (80 mL), brine, saturated aqueous sodium bicarbonate and brine, dried over Na$_2$SO$_4$, filtered and concentrated to dryness to yield compound 13c (5.75 g, quantitative) as a light pink foam. The structure of Compound 13c was confirmed by LCMS, $^1$H NMR and $^{19}$F NMR.

Alternate method for the Preparation of Compound 13c

Compound 7 (55 g, 52.9 mmol) and Compound 11 (94 g, 161.9 mmol, 3.06 eq.) were dissolved in dry THF (575 mL) and purged with argon. Pd(OH)$_2$/C (25 g, 20 wt %) was added and a stream of H$_2$ gas was bubbled through the solution via a balloon and a long syringe needle. The reaction was stirred vigorously for 6 hours, replenishing the H$_2$ balloon as necessary (3×). The reaction was monitored by TLC (20% MeOH in DCM) and LCMS. Upon completion the reaction mixture was filtered thru a pad of celite. The filtrate was concentrated under reduced pressure to provide a tan syrup that was dissolved in DCM (500 mL) and transferred to a separatory funnel. The reaction mixture was washed with 1:1 H$_2$O and brine (1×500 mL), then NaHSO$_4$ (0.2M, 2×500 mL), followed by H$_2$O (1×500 mL), and finally washed with brine (1×500 mL). The organics were collected, dried over MgSO$_4$, filtered and concentrated to provide the crude material as a sticky foam. The crude Compound 13b was used without further purification in the next step.

Crude Compound 13b was (138 g, 52.9 mmol theoretical) was dissolved in dry DCM (525 mL) and diisopropylethylamine (DIEA) was added (37 mL, 4 eq.). The reaction was purged with nitrogen and PFP-TFA was added slowly to the reaction mixture via syringe (18 mL, 105 mmol, 2 eq.). The color of the reaction changed from pale yellow to pale orange, and gave off a light smoke which was blown away with a stream of nitrogen. Additional DIEA was added to bring the reaction to pH=9-10 (53 mL DIEA total). The reaction was allowed to stir at room temperature for one hour, during which time the reaction turned magenta in color. Completion of reaction was confirmed by LCMS. The reaction was washed with NaHSO$_4$ (0.2M, 1×500 mL) followed by water (1×500 mL). The reaction mixture was washed with 1:1 H$_2$O and saturated aqueous NaHCO$_3$ until the level of PFP-OH was less than 10% (4×400 mL). The organic layer was collected, washed with brine (1×500 mL), dried over MgSO$_4$, filtered and concentrated to a sticky foam which was dissolved in EtOAc (150 mL). The reaction was stirred vigorously, and hexanes (500 mL) was added. A sticky white solid formed, and deposited as a gum on the walls of the flask. The reaction was allowed to sit for 20 minutes, then the solvent was decanted. The precipitation process was repeated. The resulting combined gum was dried under high vacuum to give Compound 13c (95 g, 95% from Compound 7) as a brittle white foam. The structure of Compound 13c was confirmed by LCMS, $^1$H NMR and $^{19}$F NMR.

Alternate Method for the Preparation of Compound 13b

To a 1 L pressure bottle (parr hydrogenator) was added THF (110 mL) followed by Compound 11 (25.5 g, 0.044 mol, 3.05 eq.) under nitrogen. The bottle was agitated manually for 10 minutes. To the bottle was added Compound 7 (15.0 g, 0.014 mol, 1 eq.), with the transfer completed using THF (20 mL). The bottle was purged with nitrogen and the mixture was stirred/agitated for about 15 minutes. Palladium hydroxide (Pd(OH)$_2$, 4.2 g) was added under nitrogen and the bottle was attached to the hydrogenator. The bottle was flushed with nitrogen (2×15 psi) followed by a hydrogen flush (2×15 psi). The bottle was pressurized with hydrogen (15-20 PSI) and agitated with continuous monitoring to record hydrogen uptake.

| Reaction time (min.) | H$_2$ pressure (psi) | Action |
| --- | --- | --- |
| 0 | 20 | start |
| 10 | 10 | |
| 15 | 8 | |
| 16 | 22 | repressurize to 22 psi |
| 30 | 20 | |
| 45 | 18 | |
| 60 | 18 | |
| 70 | 18 | Completion. |

At 70 minutes the reaction was worked up as no tris-PFP ester, Compound 7 was remaining by TLC. The mixture was filtered under an atmosphere of nitrogen through about a 1.5 inch tall celite bed (pre-washed with THF). The filter cake was washed THF (2×20 mL). The combined filtrate was then concentrated with warming from 30-40° C. under high vacuum to give crude Compound 13b as a semi-solid foam. The crude material was purified by silica gel column chromatography as illustrated above to provide Compound 13b (18.4 g, 81%) as a light yellow foam. The structure of Compound 13b was confirmed by LCMS and $^1$H NMR.

Example 8

Preparation of Compound 13c

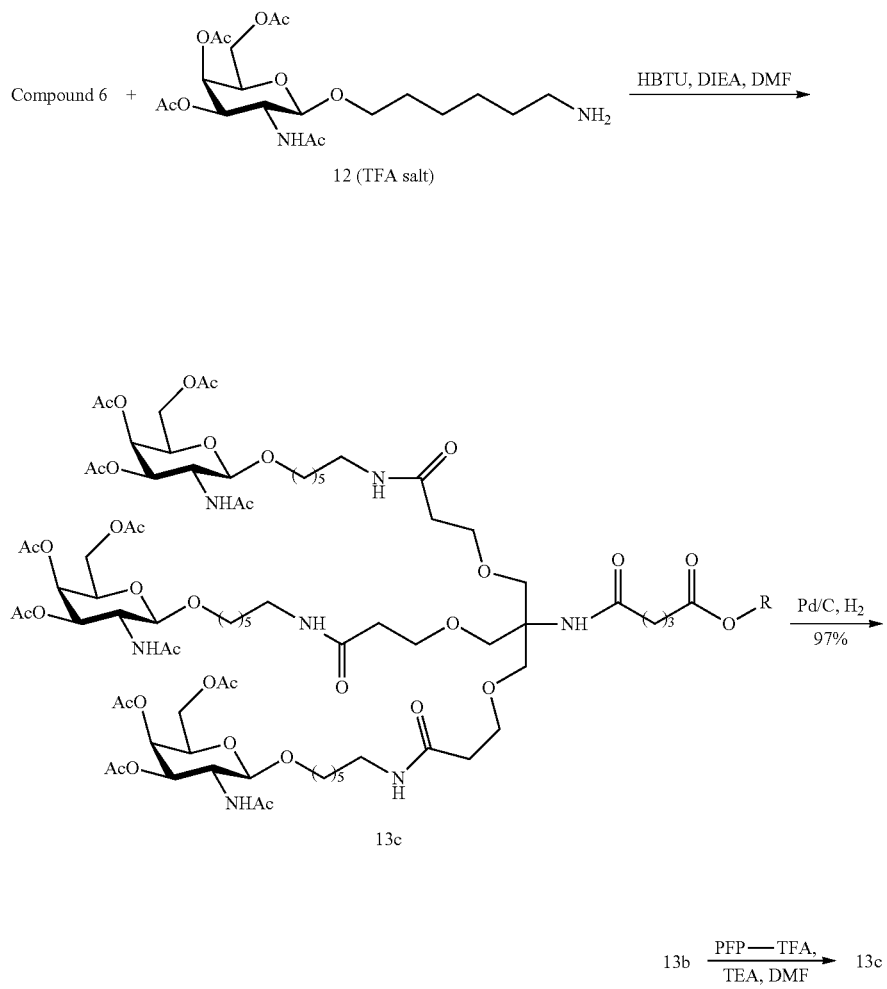

Compound 13a: R = Bn
Compound 13b: R = H
Compound 13c: R = pentafluorophenyl

Compound 6 (4.0 g), HBTU (9.8 g) and DIEA were dissolved in DMF (30 mL) and stirred at room temperature for 5 minutes. A solution of Compound 12 in DMF (12.4 g in 30 mL) was added. The reaction was stirred at room temperature and monitored by LCMS. The reaction was complete after 2 hours of stirring. The reaction mixture was concentrated under reduced pressure at 50° C. The residue was diluted with dichloromethane and resulting organic phase was washed with water, 1N NaHSO$_4$, brine, filtered and dried over anhydrous Na$_2$SO$_4$. The organic phase was concentrated to dryness and the residue was purified by silica gel column chromatography and eluted with ethyl acetate (2 CV), 2% MeOH in ethyl acetate (2 CV), 5% MeOH in ethyl acetate (4 CV), 8% MeOH in ethyl acetate (4 CV), 10% MeOH in ethyl acetate (4 CV) and 15% MeOH in ethyl acetate (8 CV). Compound 13a (11.26 g, 83%) was eluted at 10-15% methanol in dichloromethane. The structure of Compound 13a was confirmed by LCMS and $^1$H NMR.

Compound 13a (9.9 g) and Pd/C (1 g) were suspended in a mixture of methanol (20 mL) and ethyl acetate (20 mL) and hydrogenated under hydrogen atmosphere pressure (balloon). The reaction was complete after 12 hours as monitored by LC MS. The catalyst was filtered through a celite pad and celite pad was washed thoroughly using methanol/ ethyl acetate mixture (200 mL, 1:1). The combined organic solutions were concentrated to dryness to provide compound 13b (9.32 g) as a white foam. The structure of Compound 13b was confirmed by LCMS and $^1$H NMR.

Compound 13b (9.15 g) and TEA (2.2 mL, 3 eq.) were dissolved in DMF (40 mL) and PFP-TFA (1.81 mL, 2 eq.) was added (color changed from yellow to burgundy). After one hour, LCMS showed that the reaction was completed. The DMF was removed under reduced pressure at 70° C. 1N NaHSO$_4$ (100 mL) was added and the mixture was extracted with dichloromethane, washed with brine, saturated sodium bicarbonate, brine, dried over Na$_2$SO$_4$ and concentrated to dryness. Compound 13c (9.67 g) was obtained as yellow foam. The structure of Compound 13c was confirmed by LCMS, $^1$H NMR and $^{19}$F NMR.

Example 9

General Method for Conjugation of Compound 13c to Oligomeric Compound Free Amino Group (Solution Phase Conjugation)

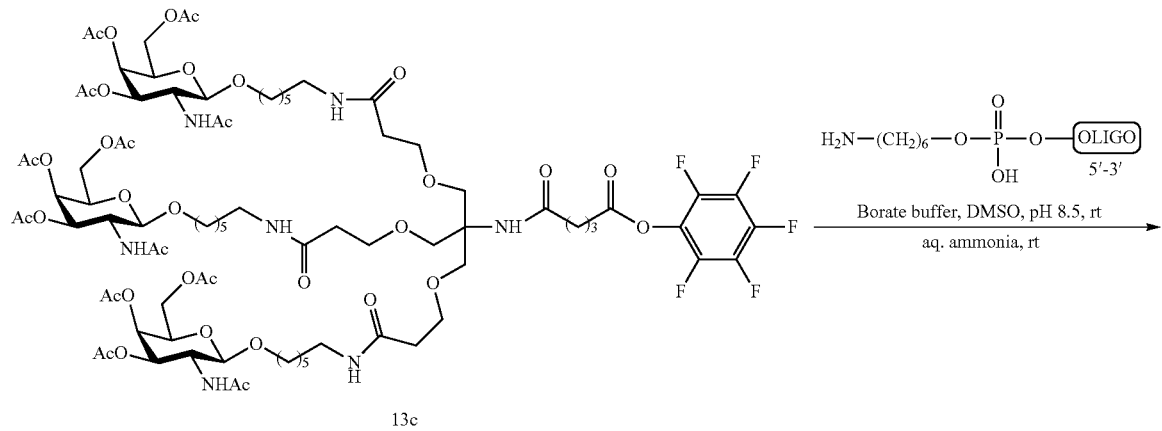

13c

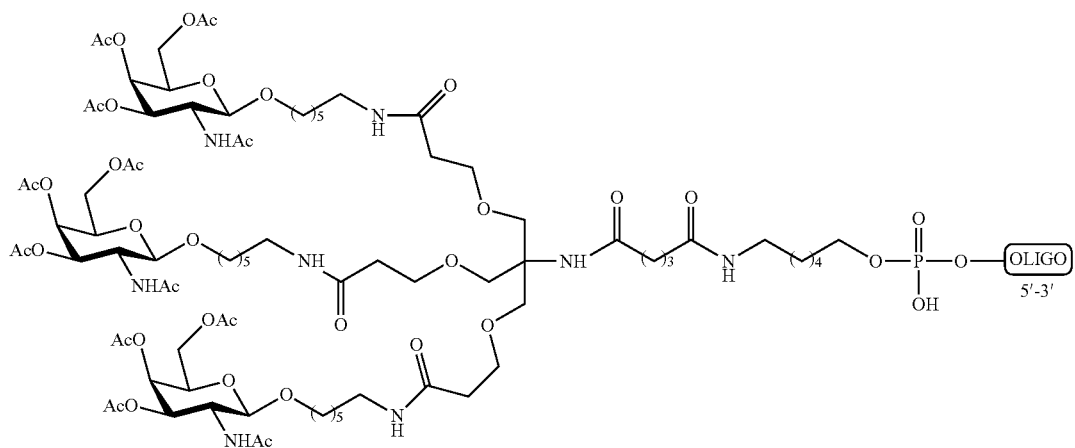

The solution phase conjugated oligomeric compound is prepared as per U.S. Pat. No. 9,127,276, issued on Sep. 8, 2015, see Example 46. The 5'-hexylamino modified oligomeric compound is first synthesized as the MMT-protected hexylamino then, purified, deblocked and reacted with the THA conjugate group which requires further purification.

Example 10

Preparation of Compound 14

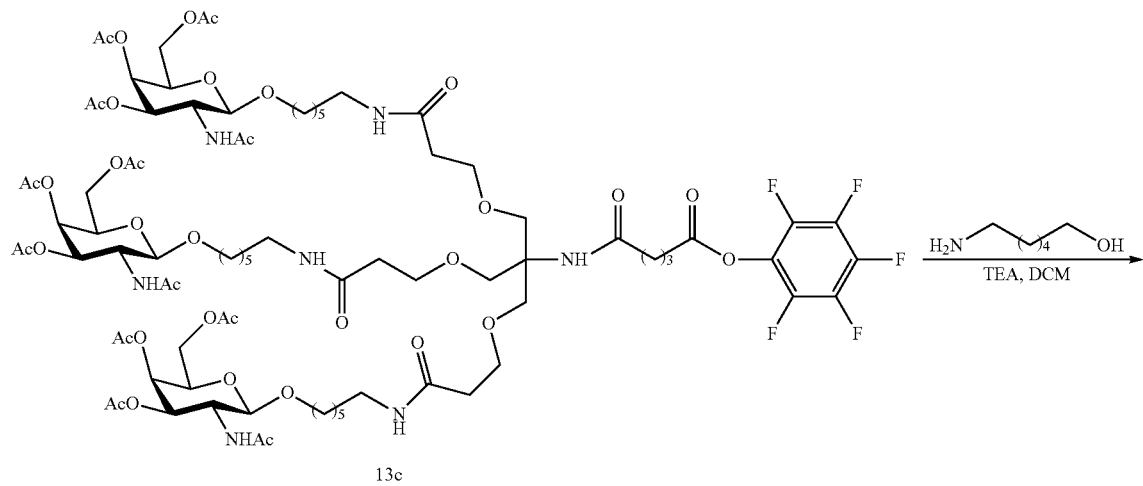

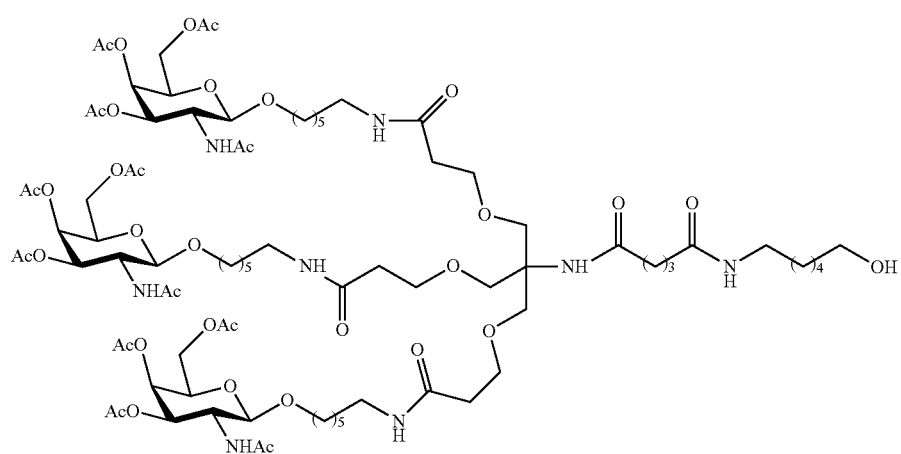

To a solution of Compound 13c (10 g, 5.3 mmol), TEA (1.47 mL, 10.5 mmol) in dichloromethane (40 mL), 6-amino-1-hexanol in dichloromethane (10 mL) was added dropwise. After stirring at room temperature for 12 hours the reaction mixture was concentrated and the residue was purified by silica gel column (Biotage Silica Gel Colum Chromatography, 220 g) and eluted with 5-20% MeOH in dichloromethane to yield Compound 14 (9.1 g, 94%). LR MS (ESI) calcd for $C_{84}H_{139}O_{36}N_8[M+H]+m/z=1837.1$, found 1837.9.

Example 11

Preparation of Compound 15

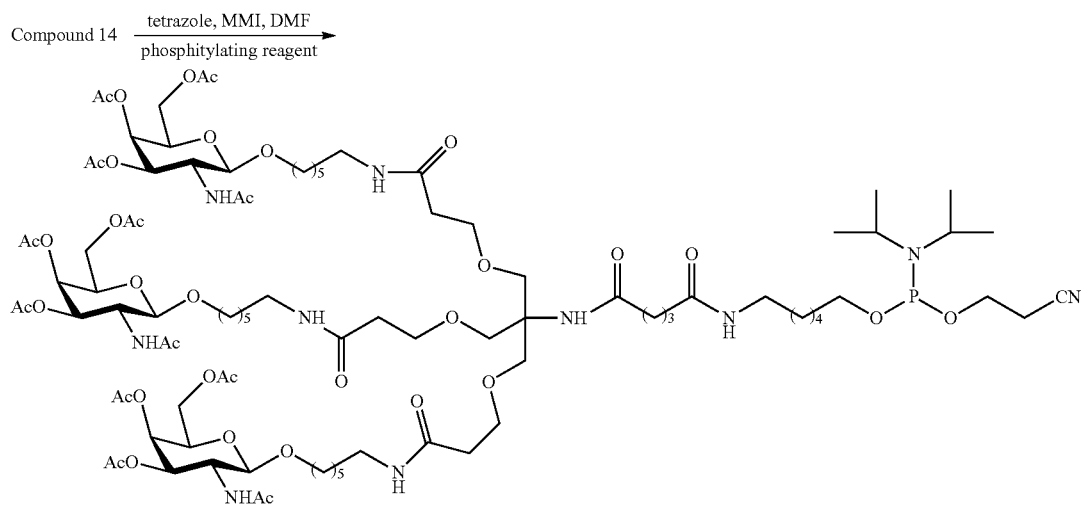

To a DMF (25 mL) solution of Compound 14 (8.96 g, 5.0 mmol) and tetrazole (0.273 g, 4.0 mmol) at 0° C., 1-methylimidazole (97 µL, 1 mmol) and 2-cyanoethyl N,N-tetraisopropylphosphoramidite (phosphorylating reagent, 2.3 mL, 7 mmol) were added. The reaction mixture was warmed to room temperature and stirred for 12 hours. The reaction mixture was extracted with ethyl acetate (100 mL), washed with sat. NaHCO$_3$(100 mL) and brine (100 mL), and dried over Na$_2$SO$_4$. After filtration the ethyl acetate solution was concentrated under reduced pressure. The residue obtained was purified by silica gel column chromatography and eluted first with ethyl acetate, then 50% acetone in ethyl acetate, followed by acetone and 50% acetone in THF to yield Compound 15 (7.5 g, 75%) as white foam. $^{31}$P NMR (121 MHz, CDCl$_3$): δ 147.32; LR MS (ESI) calcd for C$_{93}$H$_{154}$O$_{37}$N$_{10}$P [M–H]$^-$ m/z=2035.0, Found 2034.8.

Example 12

General Synthetic Steps for Oligonucleotide Synthesis

In certain embodiments, standard protocols for the synthetic steps and reagents used in oligomeric compound synthesis are as shown below:

| Synthesis Step | Synthesis Solution | Reagent/Solvent |
|---|---|---|
| A | Column Packing | Primer Support 5G or NittoPhase-HL solid support slurried in Acetonitrile |
| B | Detritylation | Dichloroacetic Acid/Toluene (1:9, v/v) |
| C | Detritylation Rinse | Toluene or Acetonitrile |
| D | Coupling | 0.2M Amidite in Acetonitrile |
|   | Coupling Activator | 1.0M 4,5-Dicyanoimidazole with 0.1M N-methylimidazole in Acetonitrile |
| E | Coupling Rinse | Acetonitrile |
| F | Sulfurization | 0.2M Phenylacetyl Disulfide in Acetonitrile/ 3-Picoline (1:1, v/v) aged ≥12 hours |
| G | Sulfurization Rinse | Acetonitrile |
| H | Capping A | N-methylimidazole/Pyridine/Toluene (2:3:5, v/v/v) |
|   | Capping B | Acetic Anhydride/Toluene (1:4, v/v) |
| I | Capping Rinse | Toluene or Acetonitrile |
| J | Phosphorus Deprotection | Triethylamine/Acetonitrile (1:1, v/v) |
| K | End Wash | Toluene or Acetonitrile. |

Those skilled in the art would realize that many of the reagents and or solvents can be modified or substituted from that listed above while providing comparable results. Such modified reagents are known in the art. In certain embodiments, automated synthesis is performed as per the above steps with modification or substitution of one or more of the solid support material, detritylation reagents, rinse or wash solvents, activator reagents, amidite solution, sulfurization reagent, capping reagents (A and or B) or deprotection reagents. In general, the equivalents are essentially the same for each modified synthesis wherein the main differences are in the solvents and or types of reagents used such as for example differences in capping reagents (5% to about 10% acetic anhydride, from about 5% to about 10% N-methylimidazole and from about 5% to about 15% pyridine or from about 5% to about 10% 2,6-lutidine dissolved in tetrahydrofuran, toluene or acetonitrile). Other examples include different types of sulfurizing reagents available and or replacement of the sulfurization reagent which produces a phosphorothioate internucleoside linkage with an oxidizing reagent to produce a phosphodiester linkage.

In certain embodiments, the capping step is performed at a reduced amount or skipped altogether (see U.S. Patent Publication No.: US 2015/0218205). In certain embodiments, coupling conditions are modified for specific nucleosides (see U.S. Patent Publication No.: US 2015/0368288).

Example 13

General Method for Solid Phase Synthesis of Oligomeric Compounds

In certain embodiments, standard protocols for preparing oligomeric compounds on a solid phase medium is performed as outlined below:

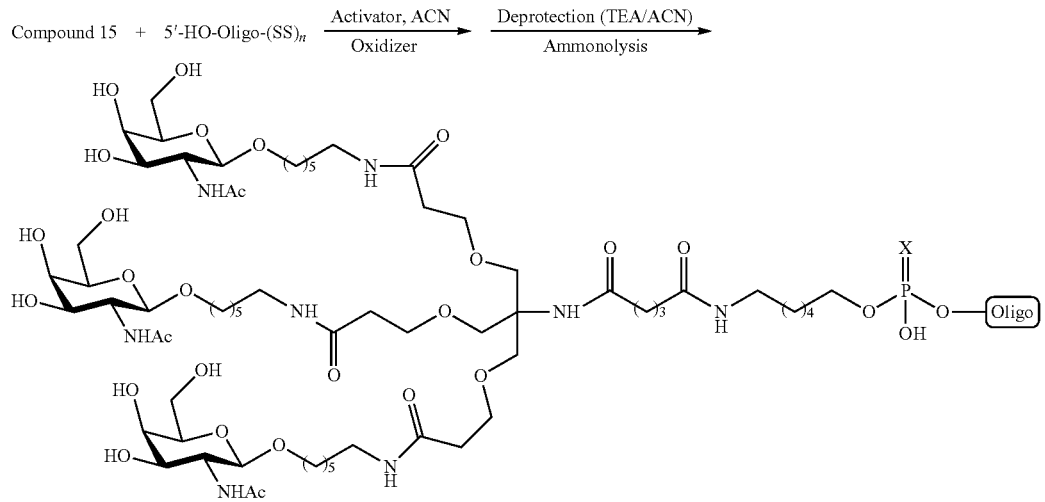

a) providing a synthesis column packed with a solid support having a plurality of blocked hydroxyl groups;

b) contacting the solid support with a deblocking solution to provide free hydroxyl groups;

c) contacting the solid phase with one or more solvents to wash the solid phase;

d) contacting the solid phase with a coupling mixture by simultaneously contacting the solid phase with equal volumes of a solution containing a selected monomer subunit capable of forming a phosphite intermediate and a solution containing an activator;

e) recontacting the solid phase with the coupling mixture one or more times by recirculating the coupling mixture through a recirculation loop;

f) contacting the solid phase with one or more solvents to wash the solid phase;

g) contacting the solid phase with an oxidizing or sulfurizing solution;

i) contacting the solid phase with one or more solvents to wash the solid phase;

j) contacting the solid phase with a capping mixture by simultaneously contacting the solid phase with equal volumes of a solution containing a acetic anhydride and a solution containing a base such as dicyanoimidazole;

k) contacting the solid phase with one or more solvents to wash the solid phase;

l) repeating steps b) through k) to prepare the oligomeric compound.

To obtain the purified oligomeric compound the support bound fully protected oligomeric compound is generally base deprotected and cleaved from the solid support by heating and treating with a solution of ammonium hydroxide. The DMT on product is then generally purified by reverse phase column chromatography. Further purification can be performed by several methods such as precipitation. Detritylation is generally performed using glacial acetic acid.

Example 14

General Method for Conjugation of Compound 15 to Oligomeric Compound Primary Hydroxyl Group (Solid Phase Conjugation)

Solid support bound oligomeric compound is detritylated following standard protocols for oligonucleotide synthesis to provide the free 5'-hydroxyl group which is then treated with Compound 15 and an activator in a suitable solvent such as acetonitrile (ACN). The resulting phosphite linked conjugated oligomeric compound is oxidized (X=O or S, dependent on oxidizer) to provide the phosphate or thiophosphate linked conjugated oligomeric compound.

Example 15

Preparation of THA Conjugated ISIS-681257

ISIS-681257 was synthesized on an automated synthesizer following standard oligo coupling protocols on a 1.1 mmol scale using NittoPhaseHL Unylinker solid support (317 µmol/g). After the 20 mer had been assembled on the solid support the 5'-trityl group was removed (10% DCA/toluene) to provide the free hydroxyl group. Compound 15 (1.75 eq., 0.2 M solution in acetonitrile) is dried over molecular sieves for 24 hours and delivered simultaneously (50%/50%, v/v) with 1 M 4,5-dicyanoimidazole and 0.1 M N-methyl imidazole in acetonitrile. The coupling solution was recirculated for 5 min. The solid support bound intermediate was oxidized with iodine in pyridine/water (0.05 M iodine in pyridine/water 90:10). The coupling, recirculating and oxidation steps were repeated two additional times (for a total of three cycles). The resulting conjugated oligomeric compound was treated with 20% diethylamine in toluene (45 min) to remove phosphorus protecting groups followed by treatment with aqueous ammonia (28-30 wt %) in water to remove protecting groups and cleave the conjugated oligomeric compound from the solid support. The cleaved conjugated oligomeric compound was diluted with water and purified by HPLC on a strong anion exchange column (GE Healthcare Bioscience, Source 30Q, 30 µm, 2.54×8 cm, A=100 mM ammonium acetate in 30% aqueous $CH_3CN$, B=1.5 M NaBr in A, 0-60% of B in 28 column volume, flow 14 mL min$^{-1}$). The fractions containing full length oligonucleotides were pooled together and desalted by HPLC on reverse phase column to yield the 5'-THA conjugated oligomeric compound. The 5'-THA conjugated oligomeric compound was characterized by ion-pair-HPLC-MS analysis with Agilent 1100 MSD system (spectra consistent with structure).

Seq Id NO. Composition (5' to 3')
ISIS-681257  THA$_o$-TeGeo$^m$CeoTeo$^m$-Ceo$^m$CGTTGGTG$^m$CTTeoGeoTeTemCe (SEQ ID NO: 1)

Between adjacent nucleosides subscript "o" indicates a phosphodiester internucleoside linkage and all other internucleoside linkages are phosphorothioate. Each nucleoside followed by a subscript "e" is a 2'-O—(CH$_2$)$_2$—OCH$_3$ (MOE) modified ribonucleoside and all other nucleosides are 2'-deoxyribonucleosides. Each "$^m$C" indicates that this nucleoside comprises a 5-methyl cytosine nucleobase. Wherein THA$_o$- indicates a 5'-O-conjugate group having the formula:

(50%/50%, v/v) with 1 M 4,5-dicyanoimidazole and 0.1 M N-methyl imidazole in acetonitrile. The coupling solution was recirculated for 30 min. The solid support bound intermediate was oxidized with iodine in pyridine/water (0.05 M iodine in pyridine/water 90:10). The resulting conjugated oligomeric compound was treated with 20% diethylamine in toluene (45 min) to remove phosphorus protecting groups followed by treatment with aqueous ammonia (28-30 wt %) in water to remove protecting groups and cleave the conjugated oligomeric compound from the solid support. The cleaved conjugated oligomeric compound was diluted with water and purified by HPLC on a strong anion exchange column (GE Healthcare Bioscience, Source 30Q, 30 μm, 2.54×8 cm, A=100 mM ammonium acetate in 30% aqueous CH$_3$CN, B=1.5 M NaBr in A, 0-60% of B in 28 column volume, flow 14 mL min$^{-1}$). The fractions containing full length oligonucleotides were pooled together and desalted by HPLC on reverse phase column to yield the 5'-THA conjugated oligomeric compound. The 5'-THA conjugated oligomeric compound was characterized by ion-

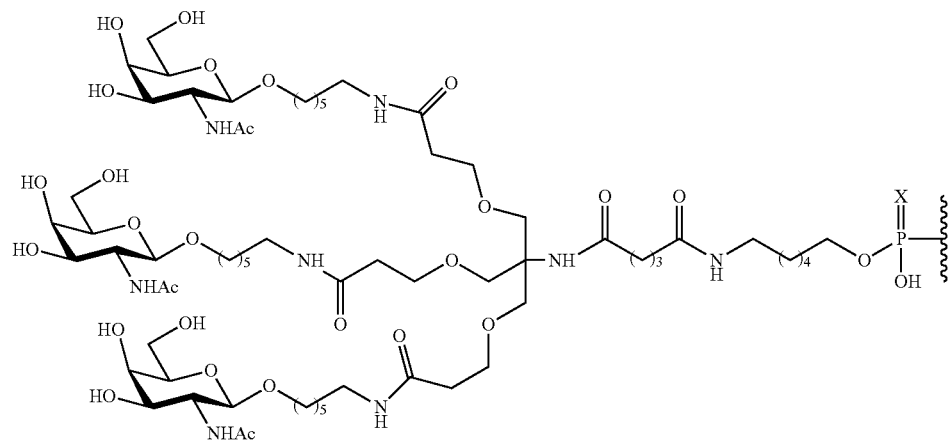

The coupling efficiency of the THA$_o$- to the oligomeric compound on separate runs was up to 90%.

Example 16

Preparation of THA Conjugated ISIS-681257

ISIS-681257 was synthesized on an automated synthesizer following standard oligo coupling protocols on a 1.1 mmol scale using NittoPhaseHL Unylinker solid support (317 μmol/g). After the 20mer had been assembled on the solid support the 5'-trityl group was removed (10% DCA/toluene) to provide the free hydroxyl group. Compound 15 (2.88 eq., 0.2 M solution in acetonitrile) is dried over molecular sieves for 24 hours and delivered simultaneously pair-HPLC-MS analysis with Agilent 1100 MSD system (spectra consistent with structure).

Seq Id NO. Composition (5' to 3')
ISIS-681257  THA$_o$-TeGeo$^m$CeoTeo$^m$-Ceo$^m$CGTTGGTG$^m$CTTeoGeoTeTemCe (SEQ ID NO: 1)

Between adjacent nucleosides subscript "o" indicates a phosphodiester internucleoside linkage and all other internucleoside linkages are phosphorothioate. Each nucleoside followed by a subscript "e" is a 2'-O—(CH$_2$)$_2$—OCH$_3$ (MOE) modified ribonucleoside and all other nucleosides are 2'-deoxyribonucleosides. Each "$^m$C" indicates that this nucleoside comprises a 5-methyl cytosine nucleobase. Wherein THA$_o$- indicates a 5'-O-conjugate group having the formula:

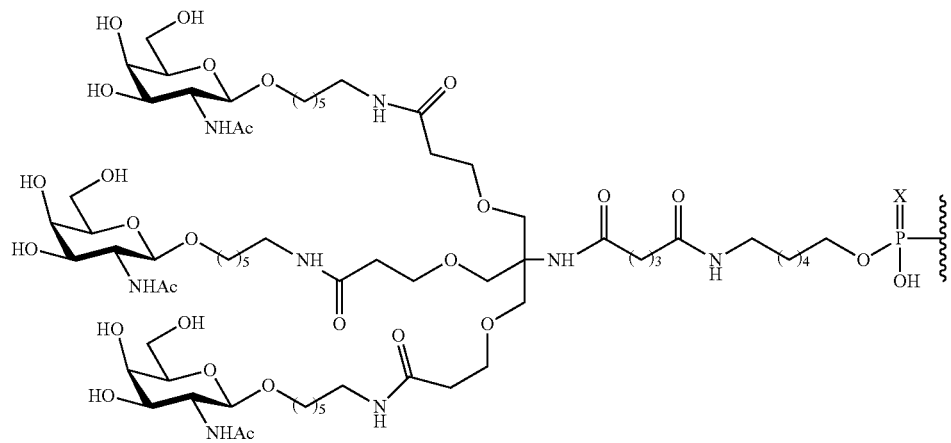

The coupling efficiency of the THA$_o$- to the oligomeric compound on separate runs was up to 90%.

Example 17

Preparation of THA Conjugated ISIS-681257

ISIS-681257 was synthesized on an automated synthesizer following standard oligo coupling protocols on a 1.1 mmol scale using NittoPhaseHL Unylinker solid support (317 µmol/g). After the 20mer had been assembled on the solid support the 5'-trityl group was removed (10% DCA/toluene) to provide the free hydroxyl group. Compound 15 was dried over molecular sieves for 24 hours and delivered simultaneously (50%/50%, v/v) with 1 M 4,5-dicyanoimidazole and 0.1 M N-methyl imidazole in acetonitrile. The solid support bound intermediate was oxidized with iodine in pyridine/water (0.05 M iodine in pyridine/water 90:10). The resulting conjugated oligomeric compound was treated with 50% triethylamine in acetonitrile (45 min) to remove phosphorus protecting groups followed by treatment with aqueous ammonia (28-30 wt %) in water to remove protecting groups and cleave the conjugated oligomeric compound from the solid support. The cleaved conjugated oligomeric compound was diluted with water and purified by reversed-phase chromatography. The fractions containing full length oligonucleotides were pooled together and desalted by HPLC on reverse phase column to yield the 5'-THA conjugated oligomeric compound. The 5'-THA conjugated oligomeric compound was characterized by ion-pair-HPLC-MS analysis with Agilent 1100 MSD system (spectra consistent with structure).

The coupling efficiency was determined by comparing the UV area of GalNAc-conjugated oligonucleotide to unconjugated 20-mer oligonucleotide (i.e., n-GalNAc). Overall yield was determined by comparing UV area to that of injections of a standard (WSS-681257-01).

| THA (Eq.) | Delivery (min) | Recirc. (min) | Coupling (° C.) | Coupling Efficiency (%) | Yield (%) |
|---|---|---|---|---|---|
| 1.75 | 2.0 | 15.0 | 19 | 80 | 49.7 |
| 1.75 | 2.0 | 30.0 | 21 | 87 | 57.4 |
| 1.75 | 2.0 | 30.0 | 45 | 91 | 57.2 |
| 1.75 | 2.0 | 180.0 | 21 | 94 | 55.1 |
| 1.75 | 8.0 | 180.0 | 19 | 90 | 49.8. |

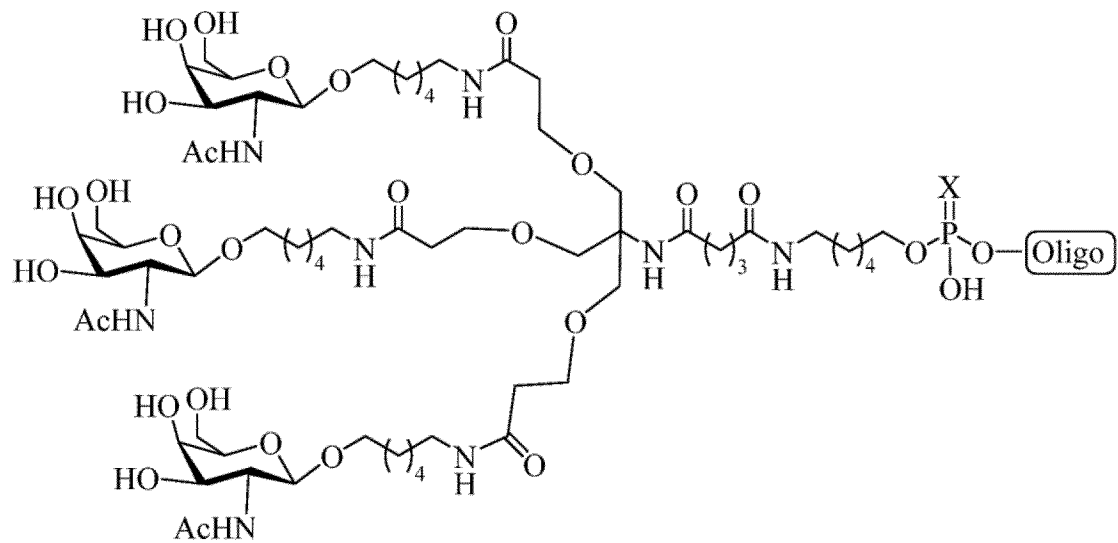

What is claimed is:

1. A method of conjugating an oligomeric compound to provide a conjugated oligomeric compound comprising:
    providing a solid support bound oligomeric compound having a primary hydroxyl group;

contacting the solid support bound oligomeric compound with a solution comprising a phosphoramidite functionalized conjugate group having the formula:

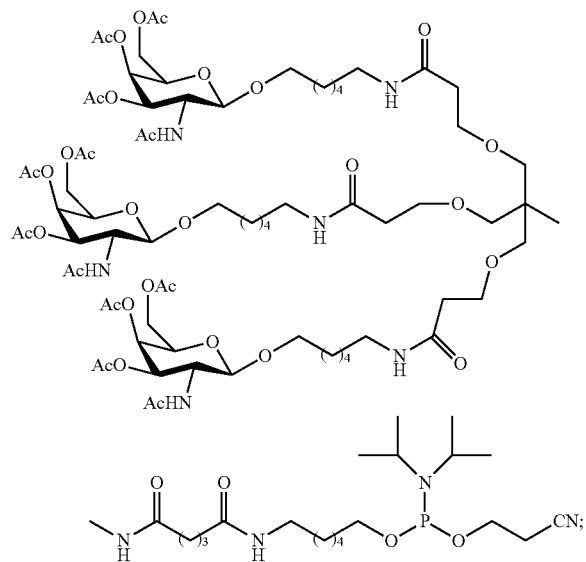

recirculating the solution to provide a phosphite linkage between the conjugate group and the oligomeric compound;
oxidizing the phosphite linkage to a phosphate or thiophosphate linkage;
treating the solid support with ammonia to provide the conjugated oligomeric compound having the formula:

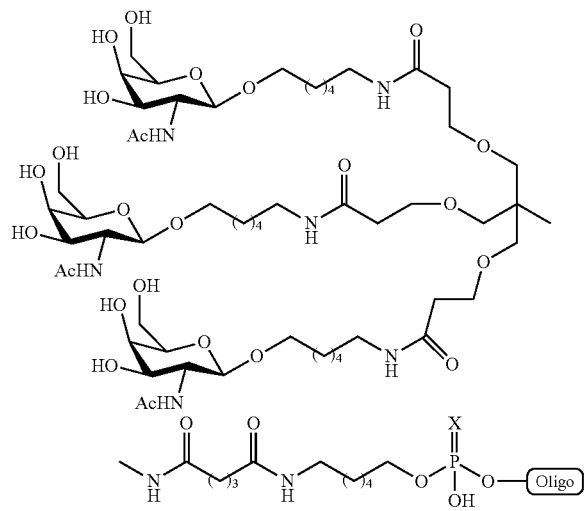

wherein X is O or S.

2. The method of claim 1, wherein the solution for the contacting step comprises from 1.5 to 2.0 equivalents of the phosphoramidite functionalized conjugate group, the steps of contacting, recirculating and oxidizing are repeated for one, two or three additional cycles and the recirculating step is performed from about 5 to about 10 minutes.

3. The method of claim 1, wherein the solution for the contacting step comprises about 1.75 equivalents of the phosphoramidite functionalized conjugate group and the steps of contacting, recirculating and oxidizing are repeated for one, two or three additional cycles.

4. The method of claim 1, wherein the solution for the contacting step comprises about 1.75 equivalents of the phosphoramidite functionalized conjugate group, the steps of contacting, recirculating and oxidizing are repeated for one, two or three additional cycles and the recirculating step is performed for about 5 minutes for each cycle.

5. The method of claim 1, wherein the solution for the contacting step comprises about 1.75 equivalents of the phosphoramidite functionalized conjugate group and the step of recirculating is performed for from 140 to 200 minutes.

6. The method of claim 5, wherein the solution for the contacting step comprises about 1.75 equivalents of the phosphoramidite functionalized conjugate group and the step of recirculating is performed for about 180 minutes.

7. The method of claim 1, wherein the conjugation of the oligomeric compound provides at least a 90% yield based on the actual number of equivalents of solid support bound oligomeric compound having a primary hydroxyl group.

8. The method of claim 1, wherein the solid support bound oligomeric compound having a primary hydroxyl group is prepared using standard solid phase protocols on an automated synthesizer.

9. The method of claim 1, wherein the contacting step is performed in the presence of 4,5-dicyanoimidazole and N-methylimidazole in acetonitrile.

10. The method of claim 1, wherein X is S.

11. The method of claim 1, wherein the oxidizing step is performed using phenylacetyl disulfide.

12. The method of claim 1, wherein the oxidizing step is performed using a solution of 0.2 molar phenylacetyl disulfide in acetonitrile:3'-picoline (1:1; v/v).

13. The method of claim 1, wherein the oxidizing step is performed using xanthane hydride.

14. The method of claim 1, wherein X is O.

15. The method of claim 1, wherein the oxidizing step is performed using iodine.

16. The method of claim 1, wherein the treatment with ammonia is performed using from about 28% to about 30% aqueous ammonium hydroxide.

17. The method of claim 1, wherein the oligomeric compound consists of from 8 to 30 linked monomer subunits.

18. The method of claim 1, wherein the primary hydroxyl group is a 5'-terminal hydroxyl group.

19. The method of claim 1, wherein the primary hydroxyl group is a 5'-terminal hydroxyl group on an optionally protected β-D-ribonucleoside, β-D-2'-deoxyribonucleoside or a modified nucleoside.

20. The method of claim 1, wherein the method is performed on at least a 200 mmol scale based on the loading of the solid support.

* * * * *

UNITED STATES PATENT AND TRADEMARK OFFICE
CERTIFICATE OF CORRECTION

PATENT NO. : 11,400,161 B2  
APPLICATION NO. : 16/332660  
DATED : August 2, 2022  
INVENTOR(S) : Isaiah E. Cedillo et al.

Page 1 of 2

It is certified that error appears in the above-identified patent and that said Letters Patent is hereby corrected as shown below:

In the Claims

In Claim 1, Column 57, Lines 5-27, the structure should read:

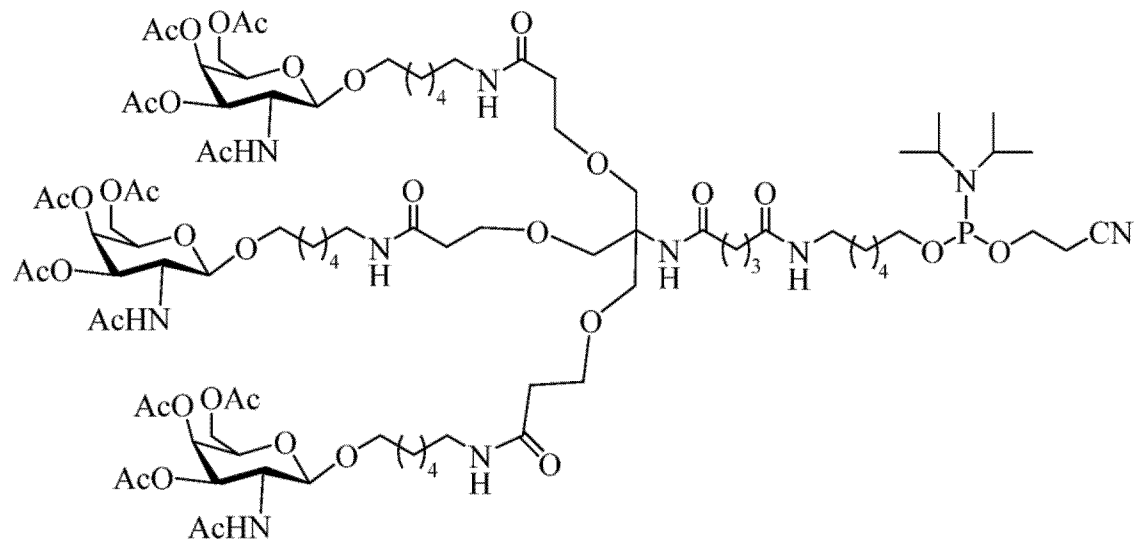

Signed and Sealed this  
Eleventh Day of October, 2022

Katherine Kelly Vidal  
*Director of the United States Patent and Trademark Office*

CERTIFICATE OF CORRECTION (continued)
U.S. Pat. No. 11,400,161 B2

In Claim 1, Column 57, Lines 37-56, the structure should read: